United States Patent
Ma

(10) Patent No.: US 11,781,114 B2
(45) Date of Patent: Oct. 10, 2023

(54) MATERIALS AND METHODS FOR EXPANSION OF STEM CELLS

(71) Applicant: FLORIDA STATE UNIVERSITY RESEARCH FOUNDATION, INC., Tallahassee, FL (US)

(72) Inventor: Teng Ma, Tallahassee, FL (US)

(73) Assignee: FLORIDA STATE UNIVERSITY RESEARCH FOUNDATION, INC., Tallahassee, FL (US)

( * ) Notice: Subject to any disclaimer, the term of this patent is extended or adjusted under 35 U.S.C. 154(b) by 392 days.

(21) Appl. No.: 16/841,218

(22) Filed: Apr. 6, 2020

(65) Prior Publication Data

US 2020/0263137 A1 Aug. 20, 2020

Related U.S. Application Data

(63) Continuation of application No. 15/120,432, filed as application No. PCT/US2015/018166 on Feb. 27, 2015, now abandoned.

(60) Provisional application No. 61/946,415, filed on Feb. 28, 2014.

(51) Int. Cl.
| | |
|---|---|
| *C12N 5/0775* | (2010.01) |
| *C12N 5/00* | (2006.01) |
| *A61K 35/28* | (2015.01) |
| *C12M 1/26* | (2006.01) |
| *C12M 1/12* | (2006.01) |
| *C12M 3/04* | (2006.01) |
| *C12M 3/06* | (2006.01) |

(52) U.S. Cl.
CPC ............ *C12N 5/0663* (2013.01); *A61K 35/28* (2013.01); *C12M 25/16* (2013.01); *C12M 27/10* (2013.01); *C12M 27/16* (2013.01); *C12M 33/00* (2013.01); *C12N 5/0062* (2013.01); *C12N 5/0075* (2013.01); *C12N 2500/02* (2013.01); *C12N 2500/42* (2013.01); *C12N 2501/33* (2013.01); *C12N 2501/39* (2013.01); *C12N 2501/727* (2013.01); *C12N 2501/998* (2013.01); *C12N 2501/999* (2013.01); *C12N 2509/00* (2013.01); *C12N 2513/00* (2013.01); *C12N 2527/00* (2013.01); *C12N 2531/00* (2013.01); *C12N 2533/30* (2013.01); *C12N 2533/54* (2013.01); *C12N 2533/70* (2013.01); *C12N 2539/10* (2013.01)

(58) Field of Classification Search
None
See application file for complete search history.

(56) References Cited

U.S. PATENT DOCUMENTS

| | | |
|---|---|---|
| 2008/0009064 A1 | 1/2008 | Ronfard et al. |
| 2010/0112691 A1 | 5/2010 | Green et al. |
| 2010/0166822 A1 | 7/2010 | Song |
| 2012/0156781 A1 | 6/2012 | Takahashi et al. |

FOREIGN PATENT DOCUMENTS

WO WO 2012/079086 6/2012

OTHER PUBLICATIONS

Liu et al., "Hypoxic preconditioning advances CXCR4 and CXCR7 expression by activating HIF-1a in MSCs", Biochemical and Biophysical Research Communications, vol. 401, pp. 509-515 (Year: 2010).*
Aggarwal, S. et al. "Human mesenchymal stem cells modulate allogeneic immune cell responses" *Blood*, Feb. 15, 2005, 105(4):1815-1822.
Alimperti, S. et al. "Serum-Free Spheroid Suspension Culture Maintains Mesenchymal Stem Cell Proliferation and Differentiation Potential" *Biotechnology Progress*, 2014, 30(4):974-983.
Amack, J.D. et al. "Knowing the Boundaries: Extending the Differential Adhesion Hypothesis in Embryonic Cell Sorting" *Science*, Oct. 12, 2012, 338:212-215.
Bartosh, T.J. et al. "Aggregation of human mesenchymal stromal cells (MSCs) into 3D spheroids enhances their antiinflammatory properties" *Proceedings of the National Academy of Sciences*, Aug. 3, 2010, 107(31):13724-13729.
Bartosh, T.J. et al. "Dynamic compaction of human mesenchymal stem/precursor cells (MSC) into spheres self-activates caspase-dependent IL1 signaling to enhance secretion of modulators of inflammation and immunity (PGE2, TSG6, and STC1)" *Stem Cells*, Nov. 2013, 31(11):1-20.

(Continued)

*Primary Examiner* — Michelle F. Paguio Frising
(74) *Attorney, Agent, or Firm* — SALIWANCHIK, LLOYD & EISENSCHENK

(57) ABSTRACT

The subject invention concerns materials and methods for expansion of stem cells, such as mesenchymal stem cells (MSC), that improve translational success of the cells in the treatment of various conditions. The subject invention utilizes cell self-aggregation as a non-genetic means to enhance their therapeutic potency in a microcarrier bioreactor. In one embodiment of the method cells are cultured in a container or vessel in the presence of thermally responsive microcarriers (TRMs) wherein cells adhere to the surface of the TRMs. After a period of time the cell culture temperature is reduced so that the cells detach from the TRMs. The detached cells are allowed to form 3D aggregates. The 3D aggregates can be collected and treated to dissociate the cells. Dissociated cells can then be used for transplantation in methods of treatment or for in vitro characterization and study.

19 Claims, 27 Drawing Sheets

(56) References Cited

OTHER PUBLICATIONS

Bhumiratana, S. et al. "Large, stratified, and mechanically functional human cartilage grown in vitro by mesenchymal condensation" *Proceedings of the National Academy of Sciences*, May 13, 2014, 111(19):6940-6945.
Chandel, N.S. et al. "Molecular Oxygen Modulates Cytochrome *c* Oxidase Function" *The Journal of Biological Chemistry*, Aug. 2, 1996, 271(31):18672-18677.
Chavakis, E. et al. "Homing of Progenitor Cells to Ischemic Tissues" *Antioxidants & Redox Signaling*, 2011, 15(4):967-980.
Chen, J. et al. "Lysophosphatidic Acid Protects Mesenchymal Stem Cells Against Hypoxia and Serum Deprivation-Induced Apoptosis" *Stem Cells*, 2008, 26:135-145.
Chen, C.-T. et al. "Coordinated Changes of Mitochondrial Biogenesis and Antioxidant Enzymes During Osteogenic Differentiation of Human Mesenchymal Stem Cells" *Stem Cells*, 2008, 26:960-968.
Chen, G. et al. "Actin-myosin contractility is responsible for the reduced viability of dissociated human embryonic stem cells" *Cell Stem Cell*, Aug. 6, 2010, 7(2):240-248.
Copland, I.B. et al. "Death and inflammation following somatic cell transplantation" *Seminars in Immunopathology*, May 1, 2011, 33:535-550.
Engler, A.J. et al. "Matrix Elasticity Directs Stem Cell Lineage Specification" *Cell*, Aug. 25, 2006, 126:677-689.
Geissler, S. et al. "Functional Comparison of Chronological and In Vitro Aging: Differential Role of the Cytoskeleton and Mitochondria in Mesenchymal Stromal Cells" *PLoS One*, 2012, 7(12):e52700(1-13).
Gonzalez-Rodriguez, D. et al. "Soft Matter Models of Developing Tissues and Tumors" *Science*, Nov. 16, 2012, 338:910-917.
Gourlay, C.W. et al. "The actin cytoskeleton: a key regulator of apoptosis and ageing?" *Nature Reviews Molecular Cell Biology*, Jul. 2005, 6:583-589.
Grayson, W.L. et al. "Effects of Hypoxia on Human Mesenchymal Stem Cell Expansion and Plasticity in 3D Constructs" *Journal of Cellular Physiology*, May 2006, 207(2):331-339.
Guo, L. et al. "Three-Dimensional Spheroid-Cultured Mesenchymal Stem Cells Devoid of Embolism Attenuate Brain Stroke Injury After Intra-Arterial Injection" *Stem Cells and Development*, 2014, 23(9):978-989.
Ingber, D.E. "Tensegrity I. Cell structure and hierarchical systems biology" *Journal of Cell Science*, 2003, 116(7):1157-1173.
Jakab, K. et al. "Tissue engineering by self-assembly and bio-printing of living cells" *Biofabrication*, Jun. 2010, 2(2):1-34.
Jayashankar, V. et al. "Integrating mitochondrial organization and dynamics with cellular architecture" *Current Opinion in Cell Biology*, 2014, 26:34-40.
Jose, C. et al. "Mitoplasticity: Adaptation Biology of the Mitochondrion to the Cellular Redox State in Physiology and Carcinogenesis" *Antioxidants & Redox Signaling*, 2013, 18(7):808-848.
Kasper, G. et al. "Insights into Mesenchymal Stem Cell Aging: Involvement of Antioxidant Defense and Actin Cytoskeleton" *Stem Cells*, 2009, 27:1288-1297.
Kelm, J.M. et al. "3D microtissue formation of undifferentiated bone marrow mesenchymal stem cells leads to elevated apoptosis" *Tissue Engineering: Part A*, 2011, 18(7/8)1-11.
Kilian, K.A. et al. "Geometric cues for directing the differentiation of mesenchymal stem cells" *Proceedings of the National Academy of Sciences*, Mar. 16, 2010, 107(11):4872-4877.
Kim, J. et al. "Bioreactor Strategy in Bone Tissue Engineering: Pre-Culture and Osteogenic Differentiation Under Two Flow Configurations" *Tissue Engineering: Part A*, 2012, 18(21-22):2354-2364.
Kim, J. et al. "Autocrine Fibroblast Growth Factor 2-Mediated Interactions between Human Mesenchymal Stem Cells and the Extracellular Matrix under Varying Oxygen Tension" *Journal of Cellular Biochemistry*, 2013, 114:716-727.
Kim, J. et al. "Endogenous Extracellular Matrices Enhance Human Mesenchymal Stem Cell Aggregate Formation and Survival" *Biotechnology Progress*, Mar. 2013, 29(2):441-451.
Krieg, M. et al. "Tensile forces govern germ-layer organization in zebrafish" *Nature Cell Biology*, Apr. 2008, 10:429-436, Supp. Information 1-5, Supp. Methods 1-6.
Lee, E.J. et al. "Spherical Bullet Formation via E-cadherin Promotes Therapeutic Potency of Mesenchymal Stem Cells Derived From Human Umbilical Cord Blood for Myocardial Infarction" *Molecular Therapy*, Jul. 2012, 20(7):1424-1433.
Lee, R.H. et al. "Intravenous hMSCs Improve Myocardial Infarction in Mice because Cells Embolized in Lung Are Activated to Secrete the Anti-inflammatory Protein TSG-6" *Cell Stem Cell*, Jul. 2, 2009, 5(1):54-63.
Li, W.Y. et al. "Mesenchymal Stem Cells for Ischemic Stroke: Changes in Effects After Ex Vivo Culturing" *Cell Transplantation*, 2008, 17:1045-1059.
Maître, J.-L. et al. "Adhesion Functions in Cell Sorting by Mechanically Coupling the Cortices of Adhering Cells" *Science*, Oct. 12, 2012, 338:253-256.
Manning, M.L. et al. "Coaction of intercellular adhesion and cortical tension specifies tissue surface tension" *Proceedings of the National Academy of Sciences*, Jul. 13, 2010, 107(28):12517-12522.
McBeath, R. et al. "Cell Shape, Cytoskeletal Tension, and RhoA Regulate Stem Cell Lineage Commitment" *Developmental Cell*, Apr. 2004, 6:483-495.
Moolenaar, W.H. "Lysophosphatidic Acid, a Multifunctional Phospholipid Messenger" *The Journal of Biological Chemistry*, Jun. 2, 1995, 270(22):12949-12952.
Munoz, N. et al. "Gas chromatography-mass spectrometry analysis of human mesenchymal stem cell metabolism during proliferation and osteogenic differentiation under different oxygen tensions" *Journal of Biotechnology*, 2014, 169:95-102.
Mylotte, L.A. et al. "Metabolic Flexibility Permits Mesenchymal Stem Cell Survival in an Ischemic Environment" *Stem Cells*, 2008, 26:1325-1336.
Numasawa, Y. et al. "Treatment of Human Mesenchymal Stem Cells with Angiotensin Receptor Blocker Improved Efficiency of Cardiomyogenic Transdifferentiation and Improved Cardiac Function via Angiogenesis" *Stem Cells*, 2011, 29:1405-1414.
Oberlender, S.A. et al. "Expression and functional involvement of N-cadherin in embryonic limb chondrogenesis" *Development*, 1994, 120:177-187.
Parekkadan, B. et al. "Mesenchymal Stem Cells as Therapeutics" *Annu Rev Biomed Eng*, Aug. 15, 2010, 12:87-117.
Pastrana, E. et al. "Eyes Wide Open: A Critical Review of Sphere-Formation as an Assay For Stem Cells" *Cell Stem Cell*, May 6, 2011, 8(5):486-498.
Potapova, I.A. et al. "Culturing of Human Mesenchymal Stem Cells as Three-Dimensional Aggregates Induces Functional Expression of CXCR4 That Regulates Adhesion to Endothelial Cells" *The Journal of Biological Chemistry*, May 9, 2008,283(19):13100-13107.
Puig, F. et al. "Stiffening and Contraction Induced by Dexamethasone in Alveolar Epithelial Cells" *Experimental Mechanics*, 2009, 49:47-55.
Quintero, O.A. et al. "Human Myo19 is a novel myosin that associates with mitochondria" *Current Biology*, Dec. 15, 2009, 19(23):2008-2013.
Rodriguez, J.P. et al. "Cytoskeletal Organization of Human Mesenchymal Stem Cells (MSC) Changes During Their Osteogenic Differentiation" *Journal of Cellular Biology*, 2004, 93:721-731.
Rombouts, W.J.C. et al. "Primary murine MSC show highly efficient homing to the bone marrow but lose homing ability following culture" *Leukemia*, 2003, 17:160-170.
Sart, S. et al. "Three-Dimensional Aggregates of Mesenchymal Stem Cells: Cellular Mechanisms, Biological Properties, and Applications" *Tissue Engineering: Part B*, 2014, 20(5):365-380.
Scheller, J. et al. "The pro- and anti-inflammatory properties of the cytokine interleukin-6" *Biochimica et Biophysica Acta* 1813, 2011, 877-888.
Sheng, Z.-H. et al. "Mitochondrial transport in neurons: impacton synaptic homeostasis and neurodegeneration" *Nature Reviews Neuroscience*, 2012, 13(2):77-93.

(56) References Cited

OTHER PUBLICATIONS

Shin, C.S. et al. "Relative Abundance of Different Cadherins Defines Differentiation of Mesenchymal Precursors Into Osteogenic, Myogenic, or Adipogenic Pathways" *Journal of Cellular Biochemistry*, 2000, 78:566-577.

Shinmura, D. et al. "Pretreatment of Human Mesenchymal Stem Cells with Pioglitazone Improved Efficiency of Cardiomyogenic Transdifferentiation and Cardiac Function" *Stem Cells*, 2011, 29:357-366.

Steinberg, M.S. "On the mechanism of tissue reconstruction by dissociated cells, I. Population kinetics, differential adhesiveness, and the absence of directed migration" *Proceedings of the National Academy of Sciences*, 1962, 48:1577-1582.

Steinberg, M.S. "On the mechanism of tissue reconstruction by dissociated cells, III. Free energy relations and the reorganization of fused, heteronomic tissue fragments" *Proceedings of the National Academy of Sciences*, 1962, 48:1769-1776.

Tigyi, G. et al. "Lysophosphatidic acid possesses dual action in cell proliferation" *Proceedings of the National Academy of Sciences*, Mar. 1994, 91:1908-1912.

Titushkin, I. et al. "Modulation of Cellular Mechanics during Osteogenic Differentiation of Human Mesenchymal Stem Cells" *Biophysical Journal*, Nov. 2007, 93:3693-3702.

Wei, L. et al. "Transplantation of Hypoxia Preconditioned Bone Marrow Mesenchymal Stem Cells Enhances Angiogenesis and Neurogenesis after Cerebral Ischemia in Rats" *Neurobiology of Disease*, Jun. 2012, 46(3):635-645.

Yeh, H.-Y. et al. "The calcium-dependent regulation of spheroid formation and cardiomyogenic differentiation for MSCs on chitosan membranes" *Biomaterials*, 2012, 33:8943-8954.

Ylöstalo, J.H. et al. "Human Mesenchymal Stem/Stromal Cells Cultured as Spheroids are Self-Activated to Produce Prostaglandin E2 that Directs Stimulated Macrophages into an Anti-Inflammatory Phenotype" *Stem Cells*, Oct. 2012, 30:2283-2296.

Ylöstalo, J.H. et al. "Unique characteristics of human mesenchymal stromal/progenitor cells pre-activated in 3-dimensional cultures under different conditions" *Cytotherapy*, Nov. 2014, 16(11):1486-1500.

Yu, Y.S. et al. "Redistribution of Mitochondria Leads to Bursts of ATP Production During Spontaneous Mouse Oocyte Maturation" *Journal of Cellular Physiology*, 2010, 224:672-680.

Zhao, F. et al. "Low Oxygen Tension and Synthetic Nanogratings Improve the Uniformity and Sternness of Human Mesenchymal Stem Cell Layer" *Molecular Therapy*, May 2010, 18(5):1010-1018.

Zimmerman, J. A. et al. "Pre-conditioning mesenchymal stromal cell spheroids for immunomodulatory paracrine factor secretion" *Cytotherapy*, 2014, 16:331-345.

Tsai, C.C, et al. "Benefits of hypoxic culture on bone marrow multipotent stromal cells" American Journal of Blood Research, 2012, vol. 2:148-159.

\* cited by examiner

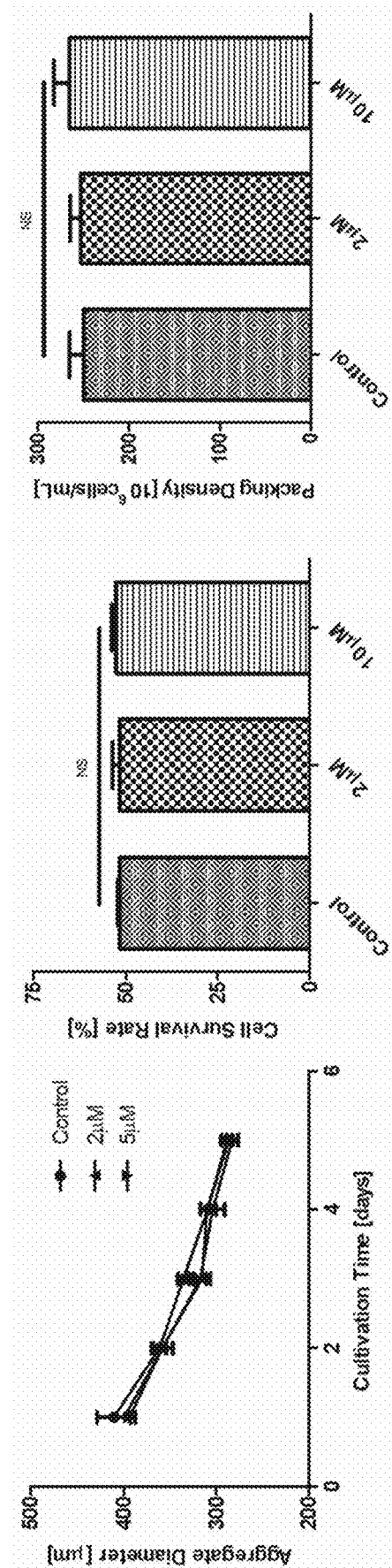

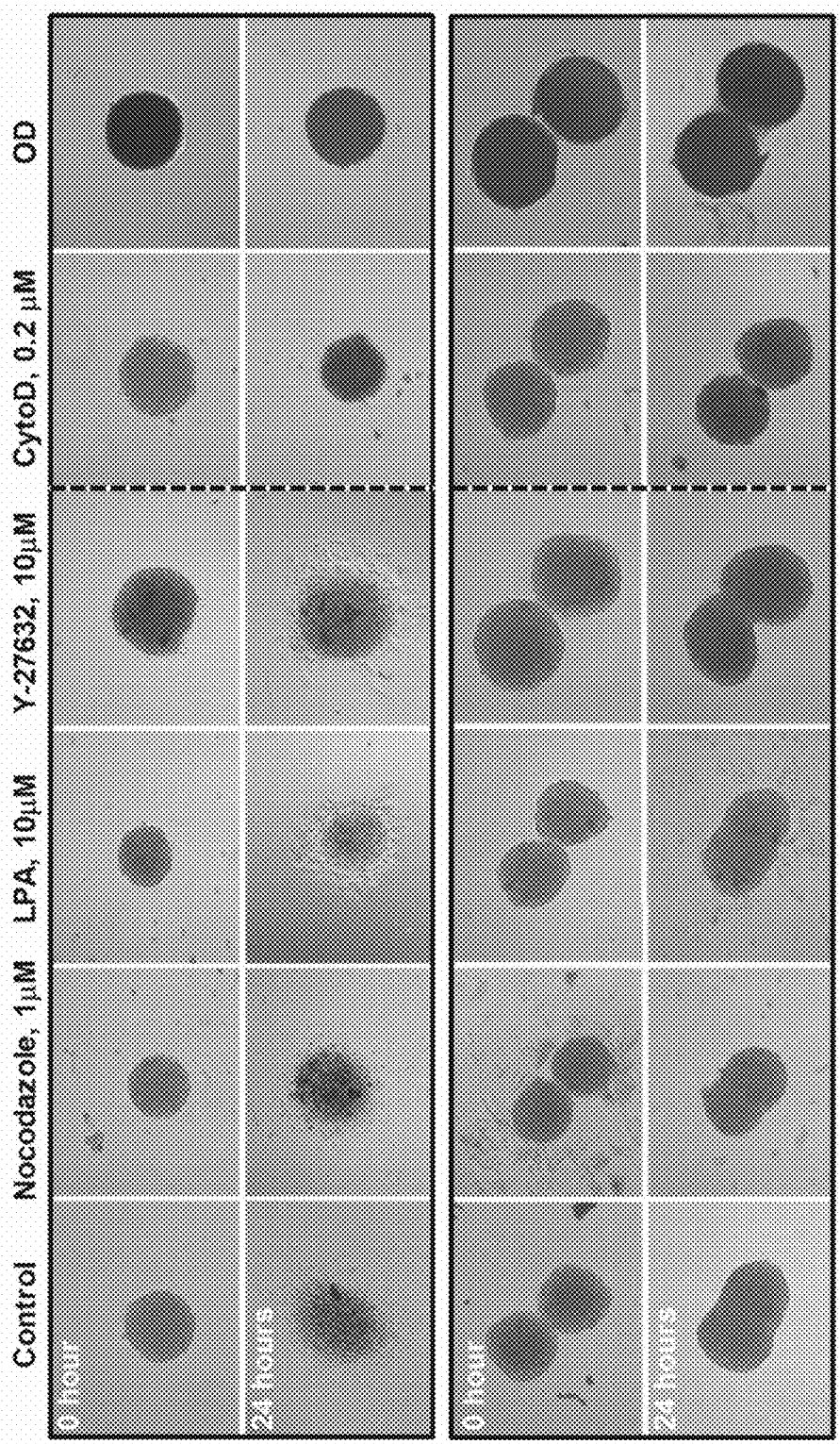
FIG. 11A Spread on glass coverslip
FIG. 11B Fusion on ULA surface

MATERIALS AND METHODS FOR EXPANSION OF STEM CELLS

CROSS-REFERENCE TO RELATED APPLICATION

The present application is a Continuation Application of U.S. Ser. No. 15/120,432, filed Aug. 19, 2016, now abandoned; which is the National Stage of International Application No. PCT/US2015/018166, filed Feb. 27, 2015; which claims the benefit of U.S. Provisional Application Ser. No. 61/946,415, filed Feb. 28, 2014, each of which is hereby incorporated by reference herein in its entirety, including any figures, tables, nucleic acid sequences, amino acid sequences, or drawings.

BACKGROUND OF THE INVENTION

Human mesenchymal stem or stromal cells (hMSCs) have been tested in over 400 clinical trials in a wide range of diseases (clinicaltrials.gov). As hMSCs translate into clinics, there is an increasing demand on technology for scalable production of therapeutically competent hMSCs in scalable bioreactor system. However, rapid hMSCs expansion has been found to induce cellular senescence and reduce their therapeutic potency. As a result, hMSC expansion technology must not only meet the demand in quantity but also preserve hMSC therapeutic potency during expansion.

Recent studies have shown that hMSC have unique properties to self-assemble into three-dimensional (3D) aggregates. The formation of 3D aggregates is beneficial for hMSC properties in several ways. First, hMSC 3D aggregation is found to activate the secretion of anti-inflammatory cytokines and other growth factors that enhance their therapeutic outcome. Second, hMSC 3D aggregation also reduces hMSC size, thereby reducing the risk for obstructing vascular system post-transplantation. Third, hMSC aggregation is a self-selection process that enhances hMSC's resistance to ischemic stress, prolonging their life-span in vivo. Finally, hMSC aggregation is a cell-mediated functional activation process that does not involve genetic materials, which facilitates their translation to clinical application. Together, these properties make hMSC aggregation an attractive method to promote hMSC viability and functions.

In the translation of hMSC-based therapy into clinics, advanced cell expansion technology is a crucial barrier that must be addressed. hMSC are rare in the bone marrow (~1 in $10^5$ mononuclear cells) and that the biomolecules released from MSC are in the range of ~10 ng based on a clinical scale mass of MSC (~$10^8$ cells), which is orders of magnitude lower than that of other biologics (Parekkadan et al. (2010)). Currently, large doses of MSC, ranging from 0.5× $10^6$/kg to 10×$10^6$/kg are required for clinical application. Transplantation of culture-expanded hMSC has very low engraftment and homing efficiency, with less than 0.001% of total injected cells survived and homed to the ischemic cortex in rats. Thus, ex vivo expansion needs not only expand cell population but also preserve their innate properties. However, it has been well-documented that expansion of hMSC in adherent culture is associated with gradual loss of chemokine receptors such as CXCR4, decreases in MSC's responsiveness to stimuli and migratory capacity, reduced cytokine secretion, increased senescence, and an increase in cell size with reduced mobility (Rombouts et al. (2003)) (Li et al. (2008)) (Copland et al. (2011); Chavakis et al. (2011)). Therefore, advanced cell expansion technology that maintains hMSC properties in a regulatory-compliant bioreactor system is crucial for hMSC's translational success.

To mitigate the culture-induced changes in hMSC properties, strategies from genetic engineering to pharmacological and hypoxic preconditioning have been actively pursued to maintain or augment hMSC therapeutic potency. For example, pre-treatment of MSC with growth factors or pharmacological drugs have shown to increase cell secretory properties, in vivo persistence, and functional recovery in ischemic stroke or cardiac injuries (Numasawa et al. (2011); Shinmura et al. (2011)). Additionally, hypoxic pre-conditioning of MSC by short-term exposure to sub-lethal hypoxia (0.5% $O_2$) has been shown to improve therapeutic outcomes of stroke animals by initiating a wide spectrum of actions, including increased expression of trophic factors such as BDNF and GDNF, down-regulation of inflammatory genes, and increased cell viability under ischemic stress (Wei et al. (2012)). Recent discoveries suggest that 3D hMSC aggregates, which are tightly packed cell clusters with 500-10,000 cells in each aggregate, have activated anti-inflammatory protein expression, increased resistance to ischemic stress, and increased expression of migratory cytokines such as CXCR4 (Bartosh et al. (2010); Potapova et a. (2008); Lee et al. (2012); Ylostalo et al. (2012)). Studies further demonstrated that both aggregates and aggregate-derived hMSC were more effective than hMSC from adherent cultures in modulating inflammatory reactions and improved recovery of stroke and myocardial infarction in mice (Bartosh et al. (2010); Lee et al. (2009); Guo et al. (2014)). Additionally, hMSC dissociated from the 3D aggregates are smaller in size due to compaction with about one-half the size of the adherent cells, thereby facilitating in vivo migration. In the translation of hMSC therapy to clinical treatment, preserving and enhancing hMSC's innate properties in the culturing stage and its implementation in a scalable process can significantly improve its potential in translational success because of its minimal safety and regulatory concerns.

BRIEF SUMMARY OF THE INVENTION

The subject invention concerns novel and translatable materials and methods for expansion of stem cells, such as MSC, that significantly improve the cells' translational success in the treatment of various conditions, such as ischemic cardiovascular and cerebral injuries. The subject invention utilizes cell self-aggregation in a microcarrier bioreactor as a non-genetic means to enhance stem cell therapeutic potency. The subject invention integrates a cell aggregation process in a scalable bioreactor system.

One aspect of the present invention concerns methods for expanding and growing stem cells, such as MSC, in a manner that provides for improved or enhanced therapeutic potency of the cells. In one embodiment of the method, thermally responsive microcarriers (TRMs) are utilized in conjunction with a scalable bioreactor system, such as the spinner flask bioreactor or a rocking bioreactor (e.g., WAVE BIOREACTOR™ (General Electric Healthcare Life Sciences)). Cells are cultured in a container or vessel in the presence of the TRMs wherein cells adhere to the surface of the TRMs. Once cells are adhered to the TRMs they can be cultured at a suitable temperature for cell growth and expansion, e.g., at about 37° C. After a period of time sufficient for cell growth and expansion on the TRMs, the cell culture temperature is reduced so that the cells detach from the TRMs. The detached cells can form cell clusters that are then cultured under conditions such that the clusters aggregate to form 3D aggregates. Following 3D aggregation of the cells, the 3D aggregates can be collected and treated to dissociate the cells (e.g., using enzymatic treatment, such as trypsinization). Dissociated cells can then be used for transplantation in methods of treatment or for in vitro characterization and study.

BRIEF DESCRIPTION OF THE DRAWINGS

(FIG. 2A) Enhanced FGF-2 secretion and binding with ECM under hypoxia. (FIG. 2B) hMSC exhibited increased proliferation on decellularized ECM with the highest proliferation on the hypoxic ECM. M(N): Extracellular matrix (ECM) decellularized from hMSC cultured under 21% oxygen conditions. M(H): Extracellular matrix (ECM) decellularized from hMSC cultured under hypoxia conditions. TCP: tissue culture plastics.

(FIG. 3A) Enzymatically detached hMSCs formed aggregates (EDA) on non-adherent surface. (FIG. 3B) hMSC also formed aggregates (TLA) after detachment from thermal responsive surface at 20° C. (FIG. 3C) TLAs have reduced Caspase-3/7 compared to the tissue culture plastics (TCP) and the EDAs; exposure to in vitro ischemic condition increased Caspase-3/7. (FIG. 3D) hMSC dissociated from TLAs had lower Caspase-3/7 than TCP and EDA under standard and ischemic conditions (Kim et al. (2013a)).

(FIGS. 4A and 4B) Oxygen profiles in the aggregates containing 5,000 (FIG. 4A) and 500 (FIG. 4B) cells (x, y axis are aggregate radius in meter). (FIG. 4C) Generation of a hypoxic zone in the aggregates requires a hypoxic culture environment (2% $O_2$). (FIG. 4D) Aggregates of different cell number and corresponding radius (left to right): 500 cells, 94 μm; 2000 cell, 152 μm; 5,000 cells, 224 μm. (FIG. 4E) Confocal images showed BrdU (green) incorporating cells in the TLAs of different sizes (Blue: DAPI) (Kim et al. 2013a).

(FIG. 5A). CytoD treatment prevented hMSC aggregation at high concentration. CytoD treatment reduced compaction of hMSC aggregates at low concentration and there is no significant difference in compaction between (FIG. 5B) 2D-pretreated and (FIG. 5C) 3D-treated aggregates. (FIG. 5D) Dose-dependent decline of aggregate diameters following 3D-treatment. However, 0.6 μM cytoD 3D-treatment significantly reduced cell viability (FIG. 5E) and packing density (FIG. 5F) compared to control aggregates at day 5. *: $p<0.05$; : $p<0.01$; *: $p<0.005$; NS: No statistical difference.

(FIGS. 6A and 6B). Nocodazole-treated hMSC aggregates underwent faster compaction the control aggregates. (FIG. 6C). F-actin structure was stained with phalloidin rhodamine (red) and nuclei counterstained with DAPI (blue). Nocodazole treatment significantly altered hMSC morphology on planar surface.

FIGS. 7A-7E. LPA treatment has limited effects on hMSC aggregate survival and compaction. Both (FIG. 7A) 2D pretreatment and (FIG. 7B) 3D treatment by LPA have minimal impact on aggregate compaction. (FIG. 7C) Projected areas of the LPA-treated aggregates declined at the same rate as control. Following 5 days of LPA 3D-treatment, the LPA-treated aggregates have comparable cell survival (FIG. 7D) as well as (FIG. 7E) cell packing density as the control.

(FIG. 8C). After 5 days of treatment, cell survival in the 10 μM Y-27632 treated aggregates is lower than non-treated control. (FIG. 8D). By day 5, cell packing density of Y-27632-treated aggregates is significantly lower compared to control.

(FIG. 9A). Formation of 3D aggregates significantly increased caspase 3/7 expression compared to 2D adherent culture for all treatment groups. Treatment by pan caspase inhibitor Q-VD-OPh significantly reduced cell compaction (FIG. 9B), improved cell survival (FIG. 9C), and increased cell packing density (FIG. 9D).

FIGS. 10A-1, 10A-2, 10B, and 10C. Morphology of 3D hMSC aggregates. (FIGS. 10A-1, 10A-2). Treatment by CytoD and Y-27632 significantly altered cell morphology in the aggregates as shown by SEM images. Cells in the control aggregates spread on aggregate surface with intimate cell-cell contacts. However, both cytoD- and Y-27632-treated aggregates have large interstitial space and exhibit round morphology. (FIG. 10B). H&E staining of control aggregates showed intact cortical actomyosin outer boundary, whereas disintegrated outer boundaries were observed in the Y-27632- and CytoD-treated aggregates. (FIG. 10C). F-actin staining of the histological sections indicated discontinuous outer boundary for the Y-27632- and CytoD-treated aggregates compared to control aggregate.

FIGS. 11A and 11B. Aggregate spreading on glass coverslip (FIG. 11A) and fusion on ULA surface (FIG. 11B). Aggregates treated by nocodazole, LPA, and Y-27632 for 5 days readily re-adhered and spread on glass coverslips and fused when adjacently placed on ULA surface. Aggregates treated by cytoD for 5 days or pre-differentiated into osteoblasts did not spread on glass coverslips nor fused when placed in close contact. OD: hMSC aggregates treated with osteogenic induction medium for 7 days.

(FIG. 12F) hMSCs dissociated from aggregates have higher resistance to in vitro ischemia compared to 2D adherent control. hMSC aggregates have significantly higher levels of IL-6 (FIG. 12G) and PGE-2 (FIG. 12H) expression compared to 2D adherent control, but the elevated expressions were attenuated by Q-VD-OPh, a pan caspase inhibitor to basal levels. CytoD and Y-27632 treatment have limited effects on IL-6 and PGE-2 secretion. ND: Not detectable.

(FIG. 13A). Aggregates of 500, 2,000, and 5,000 cells/aggregate have comparable levels of intracellular ATP/cell but all are significantly lower than that of 2D adherent cells. (FIG. 13B). Formation of aggregates significantly increased TMRM mean fluorescent intensity, indicating reduced mitochondrial membrane potential.

FIG. 16F: hBMSC readily form 3D aggregates on ultra-low adhesion (ULA) plates and re-adhere and fuse with adjacent aggregates; actin inhibition by cytochalasin D abrogates these properties. FIGS. 16A-16E. 3D aggregation increased hBMSC CXCR-4 expression, migration toward SDF-1 after dissociation, and resistance to in vitro ischemia (FIGS. 16A-16C). Levels of IL-10, HGF, STC-1, PGE-2, and IL-6 are significantly higher in hASC aggregates compared to 2D control. (FIG. 16D). Hypoxia (2% $O_2$) preconditioning (HPC) increases hASC viability after 3 days of culture (FIG. 16E). **: $p<0.01$.

DETAILED DESCRIPTION OF THE INVENTION

Figure 1:
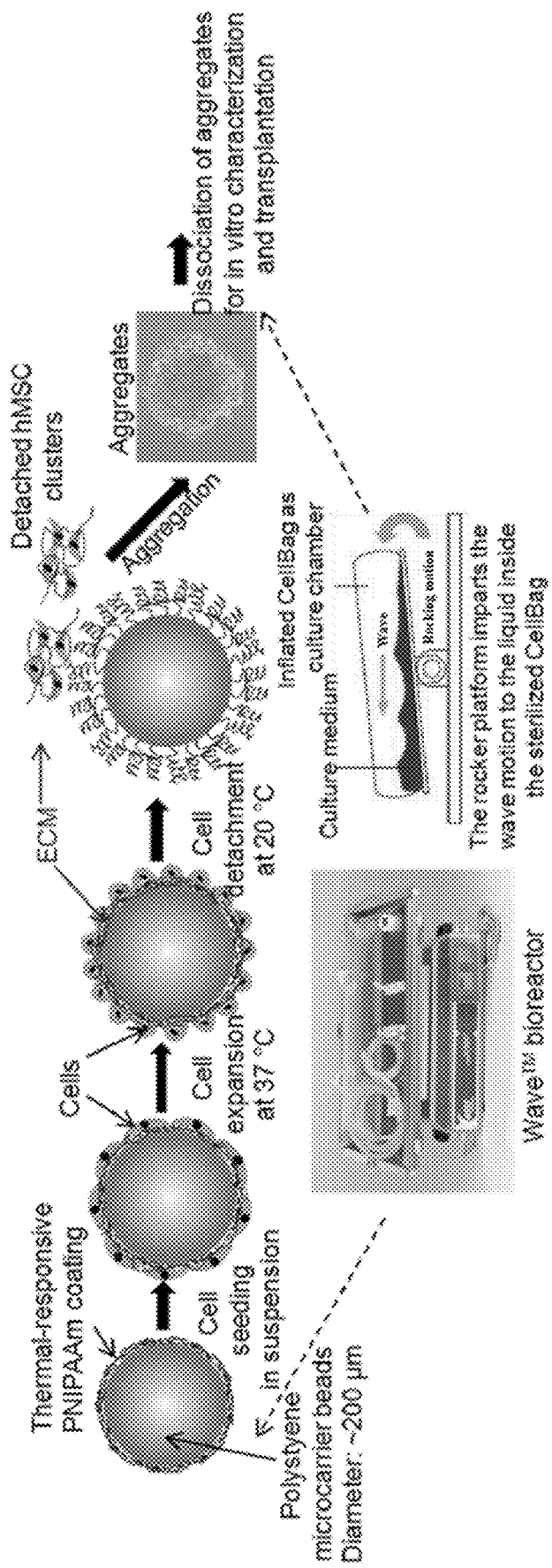
FIG. 1. Outline of the overall experimental design. The spinner flask or clinical WAVE BIOREACTOR™ (GE Healthcare Bio-Sciences Corp., Piscataway, N.J.) can be used for integrated hMSC expansion and activation using thermal responsive microcarriers (TRMs). The TRMs can be fabricated by coating commercial polystyrene microcarrier beads with thermal-responsive PNIPAAm for hMSC adhesion and expansion at about 37° C. under hypoxia in a single-use CELLBAG™ in the WAVE BIOREACTOR™. After cell expansion, bioreactor temperature is reduced to about 20° C. to detach hMSCs from the TRMs. The detached hMSC clusters coalesce and form 3D aggregates under controlled agitation or rocking and mixing condition, which promotes cell aggregation and activates hMSC secretory and migration properties. hMSC can then be dissociated for in vitro characterization and transplantation.

The subject invention concerns novel and translatable materials and methods for expansion of stem cells, such as MSC, that significantly improve the cells' translational success in the treatment of various conditions. 3D aggregation was found to activate the secretion of anti-inflammatory cytokines and other growth factors by the cells. 3D aggregation also reduces cell size, thereby reducing the risk for obstructing a vascular system. Aggregation also enhances cell resistance to ischemic stress, thereby prolonging cell life span in vivo. The subject invention integrates a cell aggregation process in a scalable bioreactor system. FIG. 1 outlines one embodiment of the present invention.

One aspect of the present invention concerns methods for expanding stem cells, such as MSC, in a manner that provides for improved or enhanced therapeutic potency. Cells for use in the invention can be isolated from a human or other animal, for example, from bone marrow and/or adipose tissue. In a specific embodiment, the cells are bone marrow MSC. In one embodiment of the method, thermally responsive microcarriers (TRMs) are utilized in conjunction with a bioreactor system, such as the spinner flask bioreactor or a rocking bioreactor, such as the WAVE BIOREACTOR™, and cells are cultured in a container or vessel in the presence of the TRMs wherein cells adhere to the surface of the TRMs. In one embodiment, the surface of the container or vessel is one that inhibits or prevents cell attachment thereto. In one embodiment, the surface is an ultra-low attachment surface, such as a surface having a hydrogel layer that is hydrophilic and/or neutrally charged. The cells and TRMs can be cultured under conditions that provide for rocking and/or agitation of the cells and TRMs in the culture system. In an exemplified embodiment, agitation or a wave motion is imparted to the cell culture system. Bioreactor systems of the invention can provide for controlled gas content (air, $O_2$, $N_2$, and/or $CO_2$), flow rates, temperature, pH, agitation rate, and circulation rate. TRMs of the invention are coated with or comprise a material that is responsive to thermal conditions, such that the material supports cell adhesion and growth at 37° C., whereas lowering the temperature to a lower critical solution temperature (LCST) causes the material to become hydrophilic and swell to the point that cells attached to the surface of the material are detached from the surface. In a specific embodiment, TRMs are polystyrene microcarrier beads comprising or coated with one or more layers of PNIPAAm. Once cells are adhered to the TRMs they can be cultured at a suitable temperature for cell growth and expansion, e.g., at about 37° C. In one embodiment, cells are cultured under hypoxic or low oxygen ($O_2$) conditions in a bioreactor system with agitation. In a specific embodiment, oxygen tension during cell culture is at about 2%. After a period of time sufficient for cell growth and expansion on the TRMs, e.g., from several hours to several days, the cell culture temperature is reduced, e.g., to about 20° C., so that the cells detach from the TRMs. In another embodiment, cells are grown and cultured in a container or vessel, wherein the surface of the container or vessel is one that inhibits or prevents cell attachment to the surface and the cells grow detached from the surface, forming clusters and aggregates. The detached cells can form cell clusters. Optionally, the TRMs can be removed from the cell culture container or vessel, or the detached cells can be transferred to another container or vessel. The detached cell clusters are then cultured at a temperature (e.g., about 37° C.) and for a period of time (e.g., several hours to days) and under conditions, such as agitation, such that the clusters aggregate to form 3D aggregates. Agitation and/or rocking of the cell container or vessel can be adjusted to promote cell aggregation. Following 3D aggregation of the cells, the 3D aggregates can be collected and treated to dissociate the cells (e.g., using enzymatic treatment, such as trypsinization). Dissociated cells can then be used for transplantation in methods of treatment or for in vitro characterization and study. In one embodiment, the dissociated cells are smaller in diameter, have higher levels of expression of CXCR-4, stronger migration to stromal cell-derived factor-1 (SDF-1), and higher resistance to ischemic stress than cells that were not from multicellular 3D aggregates.

In one embodiment of the present methods, the stem cells are cultured or grown in conditions wherein the $O_2$ tension is maintained at between about 1% and 10%. In a specific embodiment, the $O_2$ tension is maintained at between about 1% and 5%. In a more specific embodiment, the $O_2$ tension is maintained at between about 1% and 3% (e.g., $O_2$ tension could be about 1%, 2%, or 3%).

Microcarrier beads and containers or vessels utilized in the present invention can be composed of any material suitable for tissue culture, including, but not limited to, glass, polystyrene, poly(caprolactone), nylon, poly(ethylene terephthalate) (PET), gelatin, and dextran. Microcarrier beads of the invention can also comprise a material that is magnetic or can become magnetic, such as $Fe_3O_4$. Microcarrier beads of the invention can be of any suitable size and/or shape for culturing cells. In one embodiment, microcarrier beads can have a diameter of from about 50 μm to about 500 μm. In a further embodiment, microcarrier beads can have a diameter of between about 100 μm and about 200 μm.

Any container or vessel suitable for cell culture is contemplated within the scope of the invention. The container or vessel can be of any suitable size, e.g., from a few hundred milliliters in volume to 100 or more liters. In one embodiment, the container or vessel is a bag compatible with the bioreactor system, such as the CELLBAG™ (GE Healthcare Bio-Sciences Corp.). In one embodiment, the surface of the container or vessel is one that inhibits or prevents cell attachment thereto. In one embodiment, the surface is an ultra-low attachment surface, such as a surface having a hydrogel layer that is hydrophilic and/or neutrally charged. The cell culture media utilized with the present invention can be any suitable media for growth of stem cells, and can optionally comprise a low concentration of an animal serum, or can be serum-free.

In one embodiment of the present methods, a thermoresponsive material of the TRM is one that provides for cell detachment from a surface by modulating the temperature. Examples of thermoresponsive materials include, but are not limited to, polyN-isopropylacrylamide (PNIPAAm), poly(allylamine hydrochloride)-co-poly(N-isopropylacrylamide), and poly(styrene sulfonate)-co-poly(N-isopropylacrylamide), such as described in Liao et al. (2010). In one embodiment, the surface of a microcarrier comprises multiple layers of one or more thermoresponsive films. The thermoresponsive materials can optionally comprise a terminal coating of a layer of positively charged allylamine hydrochloride (PAH), or negatively charged styrene sulfonic acid (PSS), or serum, such as fetal bovine serum (FBS).

The subject invention also concerns methods for treating diseases and conditions in a person or animal by administering to the person or animal an effective amount of stem cells, such as MSC, that have been prepared using the methods of the subject invention. Cells can be administered to the person or animal using any suitable means, e.g., by injection, infusion, etc. Cells can be provided in a physiologically acceptable fluid, carrier, or buffer. Diseases and conditions contemplated for treatment using the subject invention include, but are not limited to, stroke, cardiovascular diseases, liver diseases, multiple sclerosis, graft versus host disease, diabetes, Crohn's disease, and neurodegenerative diseases. In one embodiment, the disease or condition to be treated is one associated with ischemic stress, such as ischemic cerebral (e.g., vascular dementia caused by ischemia) and cardiovascular (e.g., myocardial ischemia) diseases, or other ischemia of the bowel (large or small). In one embodiment, a human is being treated and the cells are human cells. In another embodiment, a canine animal is treated and the cells are canine cells. The cells can be autologous cells, or donor matched cells, or syngeneic or xenogeneic cells. Methods of the invention can optionally include obtaining stem cells and expanding them using the subject invention prior to administration of stem cells to the person or animal.

The methods and compositions of the present invention can be used in the treatment of humans and other animals. The other animals contemplated within the scope of the invention include domesticated, agricultural, or zoo- or circus-maintained animals. Domesticated animals include, for example, dogs, cats, rabbits, ferrets, guinea pigs, hamsters, pigs, monkeys or other primates, and gerbils. Agricultural animals include, for example, horses, mules, donkeys, burros, cattle, cows, pigs, sheep, and alligators. Zoo- or circus-maintained animals include, for example, lions, tigers, bears, camels, giraffes, hippopotamuses, and rhinoceroses.

The subject invention also concerns stem cells, such as MSC, that have been expanded and grown using a method of the present invention. In one embodiment, the cells are mammalian cells. In a specific embodiment, the cells are mammalian MSC. In a specific embodiment, the cells are human cells. In an exemplified embodiment, the cells are human MSC. The cells of the invention can be provided in a container or vessel. In one embodiment, the surface of the container or vessel is one that inhibits or prevents cell attachment thereto. In one embodiment, the surface is an ultra-low attachment surface, such as a surface having a hydrogel layer that is hydrophilic and/or neutrally charged. In one embodiment, the cells are provided in a suitable cell culture or cell storage medium. In another embodiment, cells are provided in a physiologically acceptable fluid, carrier, or buffer.

The subject invention also concerns microcarrier beads that are coated with or comprise a material that is responsive to thermal conditions. In one embodiment, a thermally responsive material utilized in the invention supports cell adhesion and growth at one temperature (e.g., 30-40° C., and typically about 37° C.) but at a lower temperature (e.g., 15-25° C., and typically about 20° C.) the material changes such that cells adhered to the material then become detached from the material. In one embodiment, the thermally responsive material becomes hydrophilic and swells at lower temperatures, thereby resulting in detachment of any cells adhered to the surface of the material. Examples of thermally responsive materials contemplated by the present invention include, but are not limited to polyN-isopropylacrylamide (PNIPAAm), poly(allylamine hydrochloride)-co-poly(N-isopropylacrylamide), and poly(styrene sulfonate)-co-poly(N-isopropylacrylamide). In one embodiment, the surface of a microcarrier comprises multiple layers of one or more thermoresponsive films. The thermoresponsive materials can optionally comprise a terminal coating of a layer of positively charged allylamine hydrochloride (PAH), or negatively charged styrene sulfonic acid (PSS), or serum, such as fetal bovine serum (FBS). Microcarrier beads of the invention can be composed of any tissue culture-compatible material, such as glass, polystyrene, poly(caprolactone), nylon, poly(ethylene terephthalate) (PET), gelatin, and dextran. Microcarrier beads can also comprise a material that is magnetic or can become magnetic, such as $Fe_3O_4$. In one embodiment, the microcarrier is a polystyrene bead. Microcarrier beads of the present invention can be of any suitable size or shape for culturing cells. In one embodiment, the microcarrier beads can have diameters of from about 50 μm to about 500 μm. In a further embodiment, a microcarrier bead of the invention can have a diameter of between about 100 μm and about 200 μm. In one embodiment, a microcarrier bead of the invention comprises a cell, such as a stem cell (e.g., hMSC), adhered to it.

The subject invention also concerns a bioreactor system comprising a cell culture vessel or container that contains TRMs of the invention. The TRMs can be present in a sterile tissue culture fluid or media that is suitable for culturing cells, such as MSC, that is contained within the culture vessel or container. In one embodiment, the bioreactor system comprises an apparatus for rocking and/or agitating the culture vessel or container. In a specific embodiment, the apparatus provides for a wave motion within the container or vessel. The container or vessel can be of any suitable size for cell culture. In one embodiment, the container can have a volume of from about 100 milliliters to 100 liters or more. In one embodiment, the surface of the container or vessel is one that inhibits or prevents cell attachment thereto. In one embodiment, the surface is an ultra-low attachment surface, such as a surface having a hydrogel layer that is hydrophilic and/or neutrally charged. The bioreactor system can also provide for controlled temperature and gas levels (e.g., $O_2$) in the container or vessel.

The subject invention also concerns articles of manufacture and kits comprising one or more containers and one or more stem cells, such as MSC, that have been prepared using the methods of the present invention. Articles of manufacture and kits can optionally comprise instructions or labeling that describes how to maintain, store, and/or use the stem cells of the invention. Articles of manufacture and kits can also optionally comprise media for storage, maintenance, and/or use of the stem cells of the invention. In one embodiment, articles of manufacture and a kit of the invention comprises a syringe suitable for injection or administration of the cells into a human or other animal. In one embodiment, the cells are MSC. In a specific embodiment, the cells are mammalian MSC. In an exemplified embodiment, the cells are human MSC.

The subject invention also concerns methods for increasing or enhancing aggregation of stem cells, such as MSC, during in vitro cell culture. In one embodiment, a method of the invention includes means for increasing actin-mediated contractility or polymerization within cells. Any means or compound for increasing or enhancing actin-mediated contractility or polymerization is contemplated within the scope of the invention. For example, compounds including, but not limited to, insulin, thapsigargin, ecdysterone, ATP, fesselin, surfactant proteins A and D, cortactin, sphingosine-1-phosphate (SIP), and jasplakinolide (JASP) are contemplated for use with the present invention. Cells can be cultured under conditions and/or in the presence of one or more compounds that increase actin-mediated contractility or polymerization in the cells. The methods for increasing or enhancing aggregation of stem cells can be used in conjunction with methods of the subject invention for expanding stem cells.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Figure 2A:
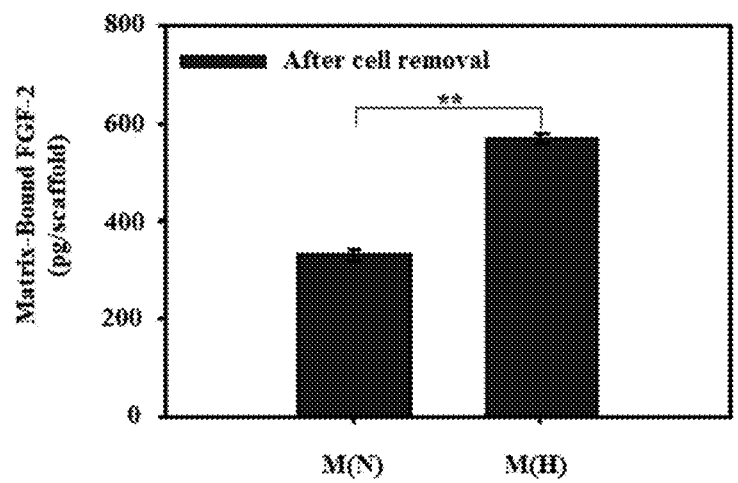
FIGS. 2A and 2B.
Figure 2B:
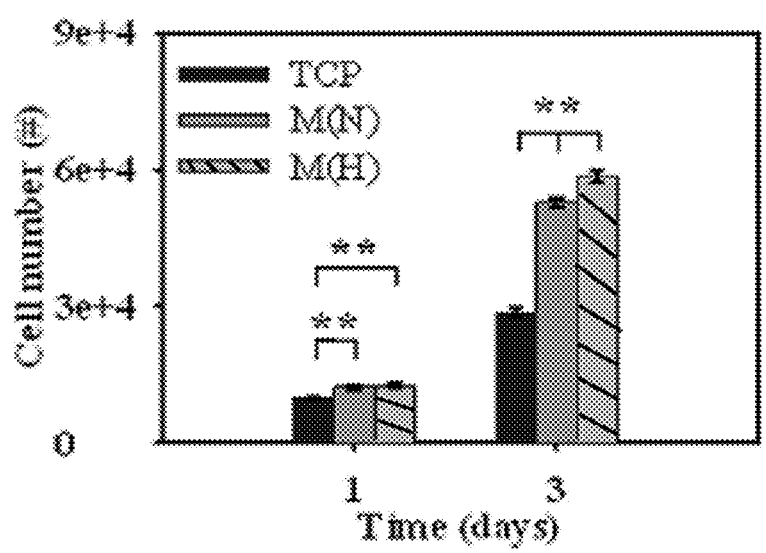
Figure 3A:
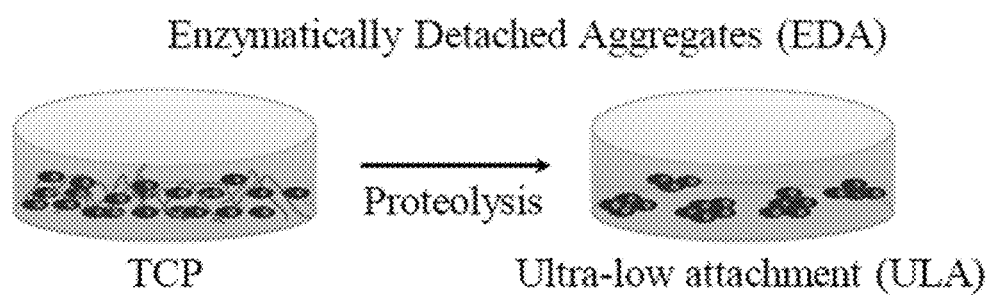
FIGS. 3A-3D.
Figure 3B:
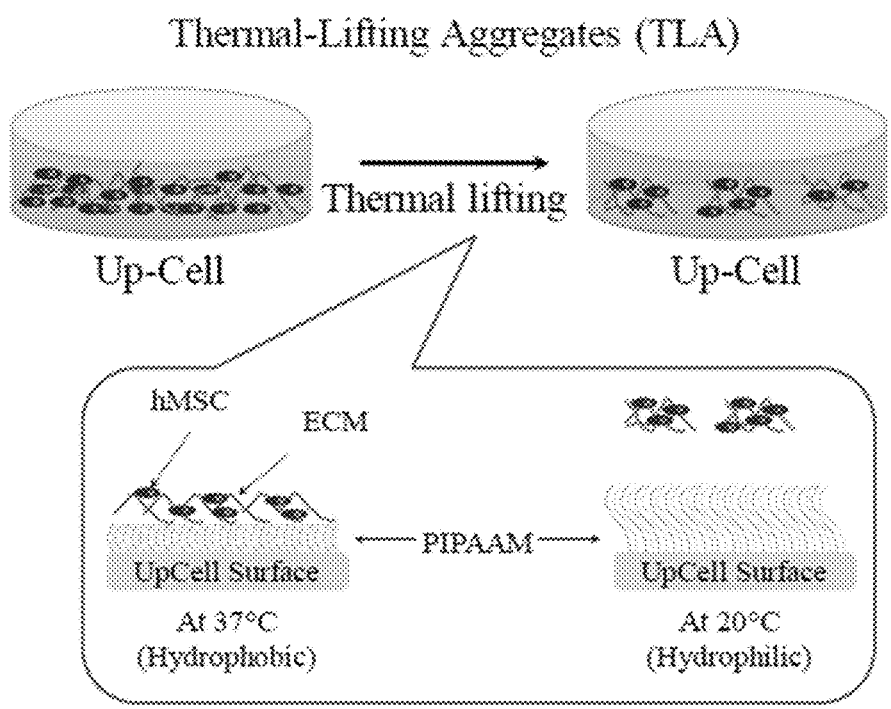
Figure 3C:
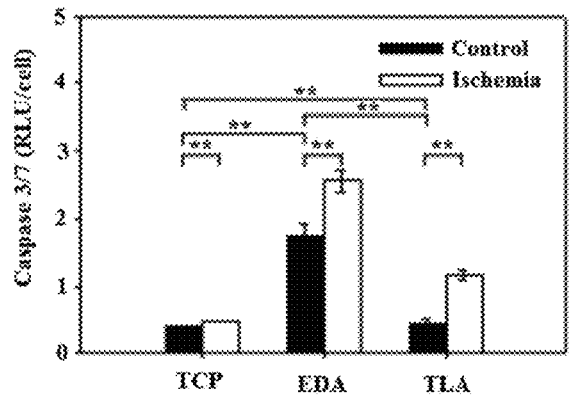
Figure 3D:
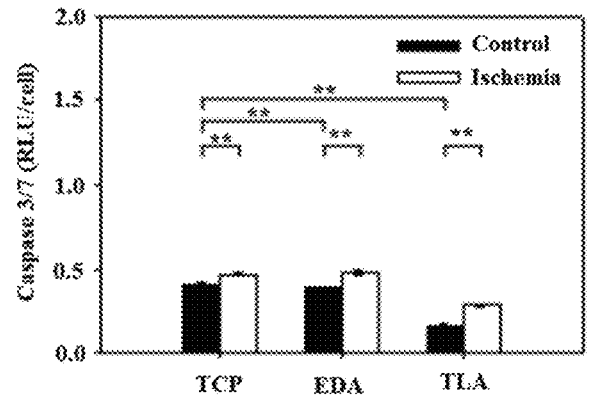
Figure 4A:
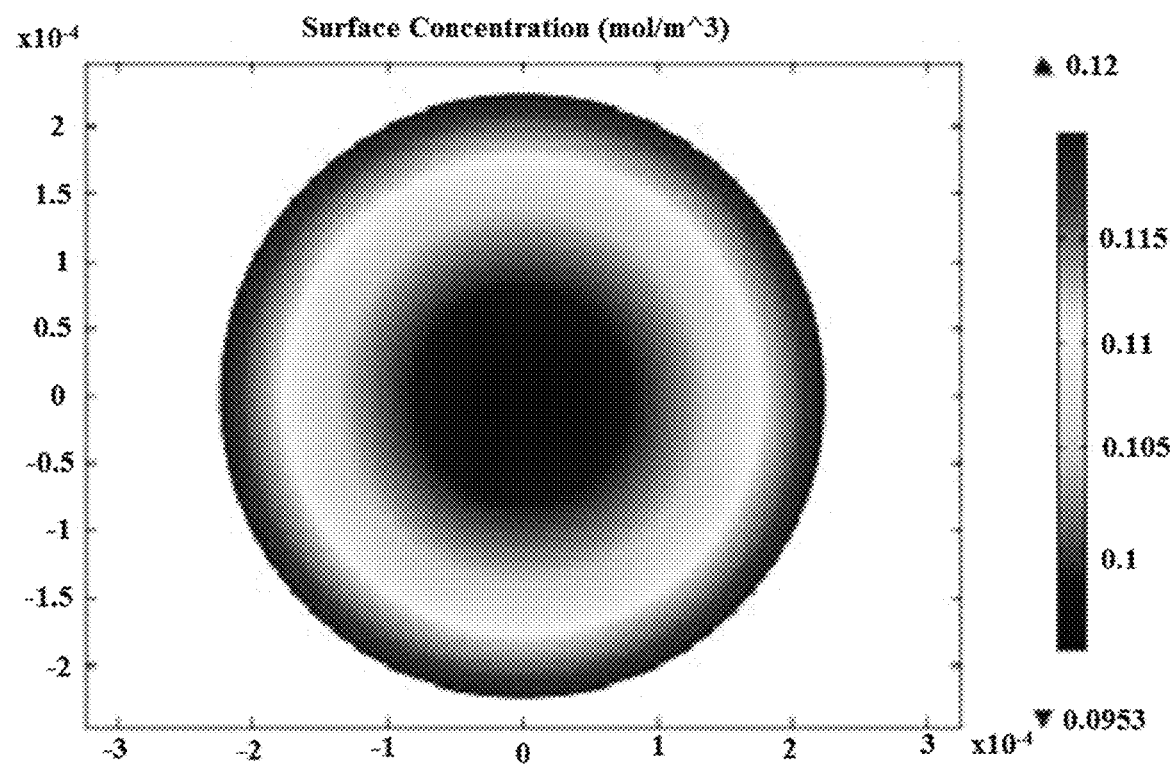
FIGS. 4A-4D.
Figure 4B:
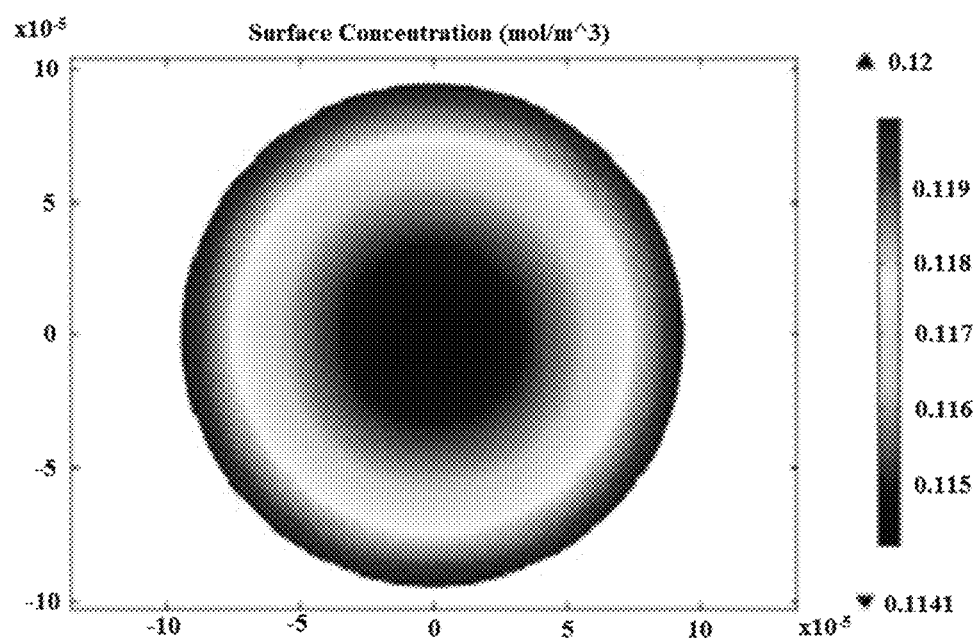
Figure 4C:
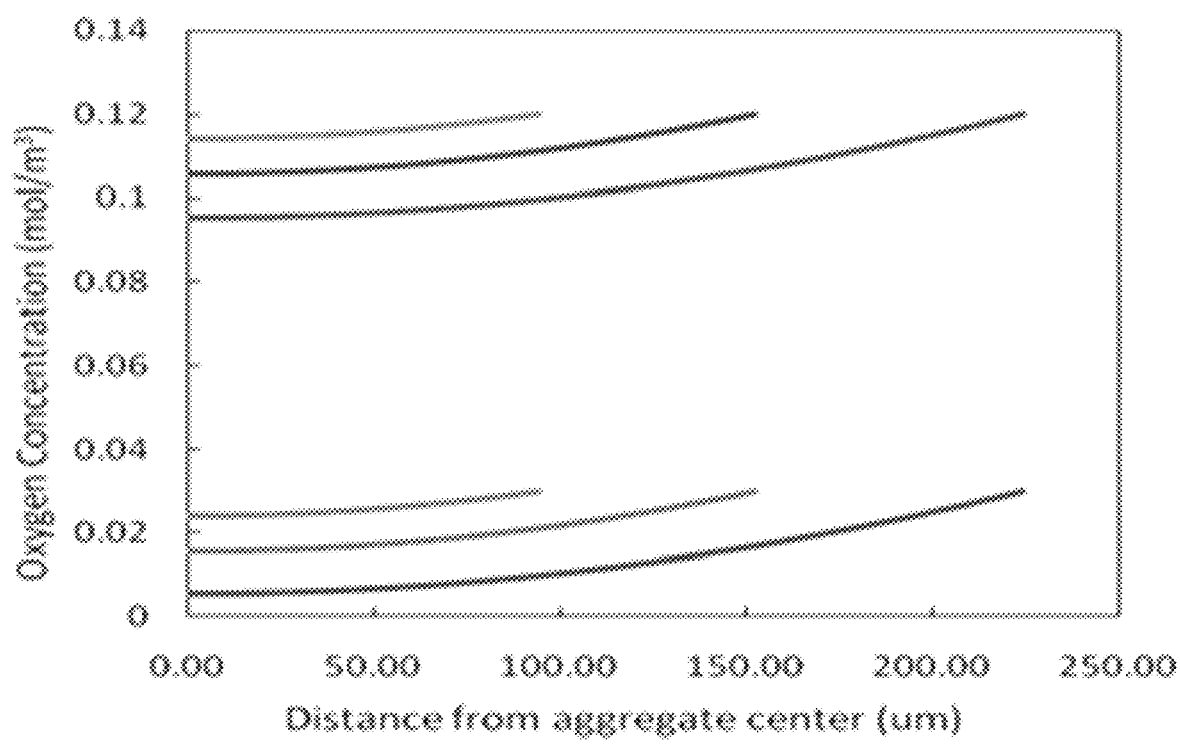
Figure 4D:
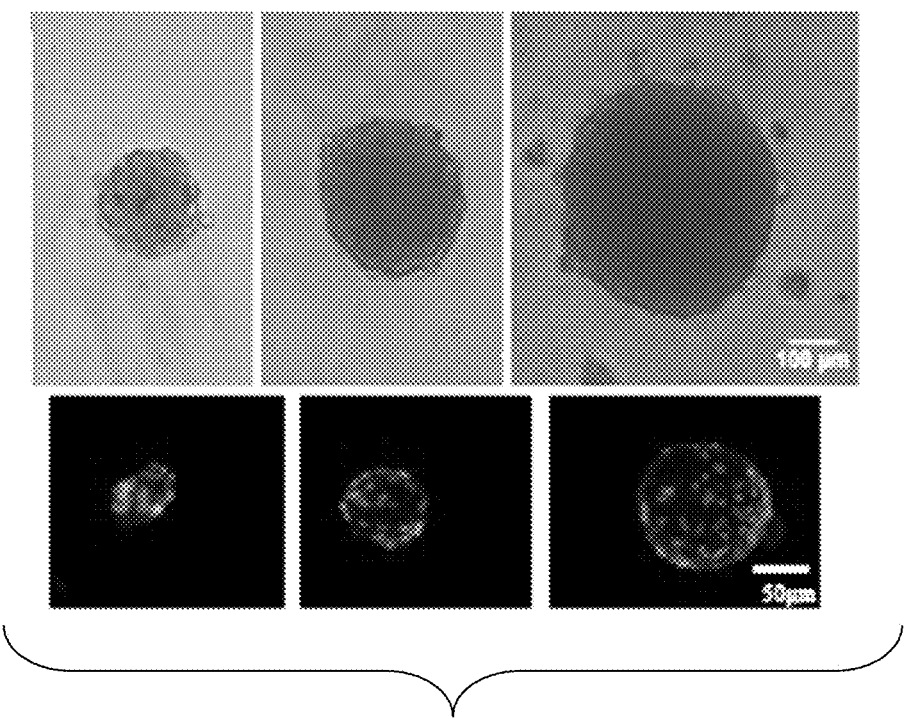

Formation of a Promitotic Microenvironment Under Hypoxia and Derivation of 3D hMSC Aggregates from Thermal Responsive Surface Hypoxic enhanced hMSC proliferation via HIF activation and stimulated secretion of ECM and endogenous FGF-2, promoting the formation of a pro-mitotic extracellular microenvironment (Grayson et al. 2007; Kim et al. 2013a) (FIGS. 2A and 2B). The 3D hMSC aggregates have been derived from thermal responsive culture plates with higher resistance to ischemic stress (FIGS. 3A-3D). Contrary to the common belief, modeling suggest a limited reduction of oxygen tension in the 3D aggregates due to low hMSC specific oxygen consumption and low cell packing density compared to tumor cells. Consequently, oxygen tension in the bioreactor can be reduced in order to create hypoxic regions in the aggregates (FIGS. 4A-4D).

Research Design and Methods:

hMSC proliferation and 3D aggregation can be achieved in a spinner flask or WAVE BIOREACTOR™ system using TRMs and combined 3D aggregation and reduced oxygen tension. The methods of the invention can restore CXCR4 functional expression and enhance hMSC secretory and migratory properties in vitro A novel bioreactor expansion strategy using TRMs in a spinner flask or a WAVE BIOREACTOR™ system is used to achieve hMSC expansion and spontaneous 3D aggregation under reduced oxygen tension in the same bioreactor system. Microcarriers have been traditionally used for scalable cell expansion such as in the WAVE BIOREACTOR™, because these beads, with diameters of 100-200 μm, provide large cell adhesion surfaces when suspended (Sharma et al. (2011)). To date, however, conventional microcarrier culture requires enzymatic cell detachment and is not conducive for cell aggregation. We have developed novel TRMs using polystyrene beads to achieve non-enzymatic cell detachment at reduced temperature (i.e., 20° C.) to induce spontaneous 3D aggregation. The outcome is a translatable protocol for hMSC expansion and functional activation in a clinical bioreactor system.

Reduced oxygen tension in the WAVE BIOREACTOR™ can stimulate hMSC proliferation and enhance their secretory properties. Our laboratory and others have shown that low oxygen tension at 2% $O_2$ (termed "hypoxia" in reference to 21% $O_2$ in a standard incubator) extended hMSC proliferation and significantly improved their multipotency and secretory functions. We have also shown that hypoxia promoted the formation of a pro-mitotic microenvironment by enhancing endogenous FGF-2 secretion and autocrine action on hMSC proliferation (Kim et al. (2013a)). Importantly, hypoxia up-regulates CXCR4 expression in MSC via HIF-1 activation (Liu et al. (2010)), and is an important mediating factor that regulates stem cell recruitment and retention.

hMSCs can self-assemble and spontaneously form 3-D aggregates in vitro in the absence of adherent surface, under mechanical forces, or within confined spaces. Importantly, MSC aggregation is a self-activation mechanism that enhances their multi-lineage differentiation potential and secretion of anti-inflammatory, pro-angiogenic, and trophic factors compared to monolayer cultures (Ylostalo et al. (2012); Bhang et al. (2011)). Among these factors, culturing hMSC as 3D aggregates significantly enhanced CXCR4 expression, migration, and adhesion to endothelial cells (Potapova et al. (2008)). To date, however, hMSC aggregates have been obtained via laboratory techniques such as hanging drop or centrifugation methods and a scalable aggregation process has yet to be demonstrated. Thus, integration of hMSC aggregation in a scalable bioreactor system, such as the clinical WAVE BIOREACTOR™, is a non-genetic strategy that effectively enhances hMSC therapeutic potential with minimal safety and regulatory concerns.

Experiments: Development of TRMs with Optimal Thickness for hMSC Expansion and Non-Enzymatic Detachment in a WAVE BIOREACTOR™ System.

A layer-by-layer sequential coating strategy previously developed in our laboratory (Liao et al. (2010)) using poly N-isopropylacrylamide (NIPAM)-based thermoresponsive polyelectrolyte multilayer (PEU) films can be used to coat commercial polystyrene microcarriers (SoloHill, Ann Arbor, Mich.). The number of PEU layers can be adjusted to control the thickness of the coating, and can be characterized following established methods (Moussallem et al. (2009); Olenych et al. (2005)). After surface characterization, hMSC adhesion and detachment can be assessed using the methods previous reported in static culture (Liao et al. (2010)). After optimizing the TRM's surface properties, the TRMs can be introduced to 0.5 L CELLBAG™ (WAVE™, GE Life Healthcare) for hMSC seeding, expansion, and aggregate formation.

P1 hMSCs can be obtained from Institute for Regenerative Medicine, Texas A&M Health Science Center and expanded following the method outlined in our prior publications (Grayson et al. (2004); Zhao et al. (2005)). hMSCs at passage 3 or 4 can be cultured in growth media on the TRMs. hMSC attachment efficiency on the TRMs is comparable with commercial microcarriers whereas the detachment efficiency after 15 minutes incubation at 20° C. may be above 95%. The impact of rocking pattern on hMSC expansion kinetics can be measured by DNA assay to quantify cell number for comparison.

Control of Oxygen Tension in the WAVE BIOREACTOR™.

Oxygen tension in the CELLBAG™ can be controlled by passing the humidified gases with premixed $O_2$, $CO_2$ and $N_2$ through the $O_2$/$CO_2$/Air mix controller. Dissolved oxygen concentration in the media can be continuously monitored using optical oxygen probes (Oxford Optronix Ltd, Oxford, UK) and controlled at, for example, 2% $O_2$, 5% $CO_2$, and balanced nitrogen (i.e., hypoxia bioreactor) or at 21% $O_2$, 5% $CO_2$ and balanced nitrogen (i.e., control bioreactor), respectively. We do not expect oxygen depletion in the aggregates because of limited oxygen consumption based on our modeling results and short culture time for aggregates.

Derivation of 3D hMSC Aggregates in the WAVE BIOREACTOR™: Influence of Temperature and Rocking Pattern.

After cell expansion, temperature in the bioreactor can be reduced to 20° C. to initiate cell detachment from the TRMs. During this process, rocking pattern can be adjusted to improve cell detachment efficiency. After cell detachment, the temperature in the WAVE BIOREACTOR™ is increased to 37° C. under continued rocking to promote re-aggregation of the detached cells. In our preliminary study (Kim et al. (2013a)), hMSC have strong tendency to re-aggregate in suspension or low adherent surface. To obtain aggregates with uniform size distribution, rocking pattern and intensity can be adjusted to promote effective and uniform cell aggregation in the bioreactor. From our preliminary study, aggregates with diameters in the range from 100 to 300 µm can be obtained. After overnight culture, the hMSC aggregates can be removed from the bioreactor and dissociated via trypsinization for in vitro characterization and transplantation.

Quantification of Cytokines and Target Gene Expressions by Real-Time PCR.

Target genes to be tested include Oct-4, CXCR-4, VEGF, FGF-2, PDGF, Akt, ERK1/2, HIF-1,2. Total RNA can be isolated from the hMSCs using the RNeasy Plus kit following the method reported in our prior publication (Grayson et al. (2007)). The expression of some of these target genes can be further validated by Western blot or ELISA following the protocol established in our lab. To characterize the activation state of ERK1/2 and Akt, phospho-specific antibodies can be used. Secreted growth factors including VEGF, BMP-2, FGF-2, and PDGF under different experimental conditions can be assayed.

In Vitro Characterization of Dissociated hMSC: Cell Viability, ROS Expression, and Flow Cytometry.

The aggregates can be dissociated in collagenase II solution (Worthington Biochemical, NJ) at 37° C. with intermittent mixing. The aggregate morphology and size can be assayed by light microscope, whereas total and spatial distribution of apoptotic cells in the aggregates can be determined by measuring Caspase-3/7 activity and by TUNEL assay. Intracellular ROS can be measured with DCFDA using a ROS Detection Kit as reported previously (Kim et al. (2013a)). Cell surface markers including CXCR-4, CD90, CD146, CD271 and cell size can be measured using flow cytometry following the method reported in our prior publication (Grayson et al. (2004)).

Materials and Methods

Culture of hMSCs.

Frozen hMSCs at passage 1 in liquid nitrogen were obtained from the Tulane Center for Stem Cell Research and Regenerative Medicine. The hMSCs were isolated from the bone marrow of healthy donors ranging in age from 19 to 49 years based on plastic adherence, being negative for CD34, CD45, CD117 (all less than 2%) and positive for CD29, CD44, CD49c, CD90, CD105 and CD147 markers (all greater than 95%), and possessing tri-lineage differentiation potential upon induction in vitro (Munoz et al. 2014). The hMSCs were expanded with minimum essential medium-alpha (α-MEM) (Life Technologies, Carlsbad, Calif.) supplemented with 1% Penicillin/Streptomycin (Life Technologies) and 10% fetal bovine serum (FBS) (Atlanta Biologicals, Lawrenceville, Ga.) on 150-mm tissue culture petri dishes (Corning, Corning, N.Y.) at a density of approximately 1,500 cells/cm$^2$ in a standard 5% $CO_2$ incubator. The culture media were changed every three days. hMSCs from three different donors at passage 5 to 7 were used in the experiments. All reagents were purchased from Sigma Aldrich (St. Louis, Mo.) unless otherwise noted.

Aggregate Formation and Treatment with Cytoskeleton Modulators.

hMSCs from monolayer culture were trypsinized and 100 µL media containing 5,000 cells were added in each well of an ultra-low attachment (ULA) 96-well plate with round-bottom (Corning, Corning, N.Y.) for overnight. To analyze size-dependent ATP contents, aggregates containing 500, 2,000, and 5,000 cells were used following the same method. Suspended single hMSCs spontaneously self-assembled into one aggregate per well. Aggregates were cultured individually up to 7 days with media change every two days. The aggregates were tracked individually and the morphologies were imaged with an Olympus IX70 microscope (Center Valley, Pa.).

Cytochalasin D (cytoD), lysophosphatidic acid (LPA), Y-27632, nocodazole were added into culture media to final concentrations of 0.2 to 0.6 µM, 2.0 to 10.0 µM, 2.0 to 10 µM, and 1.0 M, respectively. To test the temporal effects of actin modulators on aggregate formation, cells were treated with media containing cytoD and LPA during monolayer culture prior to aggregate formation (termed "2D Pretreatment") or 12 hours after aggregate formation in ULA plates (termed "3D Treatment). Only 3D treatments were performed for Y-27632 and nocodazole.

Analysis of Aggregate Size, DNA Content, Fusion, and Spreading on Adherent Surface.

Morphology of the aggregates was visualized using an Olympus IX70 microscope and the images recorded. The images were processed and the areas of the individual aggregates were calculated using ImageJ software (rsb.info.nih.gov/ij/). The DNA content of the individual aggregates was used to calculate cell number. Briefly, individually collected hMSC aggregates were washed with phosphate buffered saline (PBS) and digested with proteinase K overnight. PicoGreen (Life Technologies) was added to triplicate samples and a DNA standard in a 96-well plate. The cell numbers in aggregates were determined by the PicoGreen fluorescence intensity using 9.3 pg/cell as determined in our prior study (Kim and Ma 2012). DNA assay detects double-stranded DNA that may also be present in dead cells with intact DNA. However, this population in the aggregates is low, and the yield of live cells measured by DNA assay is close to cell count using other methods such as flow cytometry (Ylostalo et al. 2014). The packing densities were calculated using cell number divided by aggregate volume assuming a spherical shape. At least six aggregates were used in each condition.

To test re-adhesion and fusion, the aggregates from various treatment conditions were plated on glass coverslip for re-adhesion or placed adjacently on ULA surface for fusion. Images were captured with Olympus IX70 microscope and analyzed by ImageJ software.

Measurement of Caspase 3/7, Interleukin 6 (IL-6), and Prostaglandin E2 (PGE-2).

Caspase 3/7 activity was measured by Caspase-Glo 3/7 assay systems (Promega, Madison, Wis.). Caspase-Glo 3/7 working buffer was added to triplicate samples containing aggregates and culture media in 96-well LUMITRAC 200 white immunology plate (Greiner Bio-One, Monroe, N.C.). The results were read by a luminescence plate reader and normalized to cell number (Biotek Instruments, Winooski, Vt.). Secreted PGE-2 and IL-6 in conditioned media were quantified using a PGE-2 Parameter Assay Kit and IL-6 DuoSet ELISA kits, respectively (R&D Systems, Minneapolis, Minn.). Total secreted PGE-2 and IL-6 were determined by subtracting cytokine concentrations in culture media controls and normalized to the cell number in the aggregates.

Osteogenic Induction, Scanning Electron Microscopy (SEM), Immunohistochemistry, and Histology.

After aggregate formation in the ULA culture dishes, the growth media were replaced with osteogenic media (high glucose Dulbecco's modified eagle medium (DMEM) (Life Technologies) supplemented with 10% FBS, 1% Penicillin/Streptomycin, 100 nM dexamethasone, 10 nM sodium-b-glycerophosphate and 12.8-mg/l ascorbic acid-2 phosphate) following the previously reported method (Kim and Ma 2012). After 7 days of incubation, the OD-aggregates were transferred to glass coverslip for adhesion or were placed adjacently on ULA surface for fusion.

For SEM, the aggregate samples were fixed in 4% paraformaldehyde (PFA), dehydrated through a graded series of ethanol, incubated in hexamethyldisilazane, and vacuum dried overnight. The samples were mounted onto carbon-coated chucks, sputter-coated with gold in an argon atmosphere for 4 minutes at 2 kV, and analyzed on a SEM (JSM-7401F) (JEOL, Tokyo, Japan). For immunostaining, the cells were fixed with 4% PFA, permeabilized with 0.5% Triton X-100, blocked with 1.0% BSA, incubated with primary antibody, and imaged with an Olympus IX70 (Center Valley, Pa.) microscope. For histology, hematoxylin-eosin (H&E) staining was performed following the prior reported method (Kim and Ma 2012). hMSC aggregates were fixed in 10% formalin, dehydrated and embedded in paraffin wax; 10 µm sections were cut and stained with Lerner-2 Hematoxylin (Lerner Laboratories, Pittsburgh, Pa.) and Eosin-Y w/ Phloxine (Richard-Allan Scientific, Kalamazoo, Mich.) by standard procedures (Kim and Ma 2012). Images were captured with Olympus IX70 microscope with MagnaFire SP 2.1B software.

Flow Cytometry, Transwell Migration Assays, and In Vitro Ischemia.

Aggregates were dissociated in trypsin, washed in PBS, and fixed at 4% PFA at room temperature. Aliquots of 100 µL cell suspension were incubated with fluorochrome-conjugated, anti-mouse monoclonal antibody CXCR-4 (R&D Systems). For mitochondrial membrane potential measurement, trypsinized MSCs were washed by centrifugation in warm HBSS. Cell suspension was incubated with tetramethylrhodamine, methyl ester (TMRM) (Life Technologies), washed with HBSS, and analyzed by flow cytometry (BD Biosciences, San Jose, Calif.). Labeled samples were washed in PBS followed by flow cytometry analysis with the isotype controls run in parallel at the same concentration used for each antibody.

A transwell migration system (Neuro Probe, Md., USA) was used to study the migration of aggregate-dissociated hMSCs and monolayer cultured hMSCs in response to human recombinant SDF-1 (R&D systems). A cell migration assay kit using an 8-µM pore size was used. Resuspended cells in serum free medium were loaded in the top chamber of the migration well. Serum-free medium containing 30 ng/mL of SDF-1 was added to the lower chamber. Cells were incubated at 37° C. in 5% $CO_2$ for 4 hours. The remaining cells on the top chamber were scratched, and the migrated cells stained with Hoechst and counted.

To mimic ischemic conditions (IC), hMSCs dissociated from the aggregates and adherent controls were incubated in serum-free growth media at 1% $O_2$ controlled in a C-Chamber (BioSpherix, Lacona, N.Y.) for 6 h and then analyzed by Live/Dead staining (Life Technologies). The combination of serum withdrawal and low oxygen tension is known to induce hMSC apoptosis and has been used in vitro to mimic ischemic condition (Kim and Ma 2013b).

Statistics.

Unless otherwise noted, all experiments were performed at least in triplicate (n=3), and representative data were reported. Experimental results were expressed as means±standard deviation (SD) of the samples. Statistical comparisons were performed by one-way ANOVA and Tukey's post hoc test for multiple comparisons, and significance was accepted at $p<0.05$.

Following are examples that illustrate procedures for practicing the invention. These examples should not be construed as limiting. All percentages are by weight and all solvent mixture proportions are by volume unless otherwise noted.

Figure 5A:
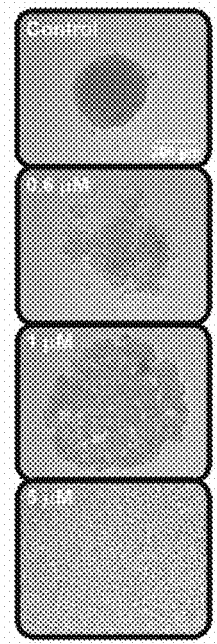
FIGS. 5A-5F. CytoD interrupts hMSC aggregation.
Figure 5B:
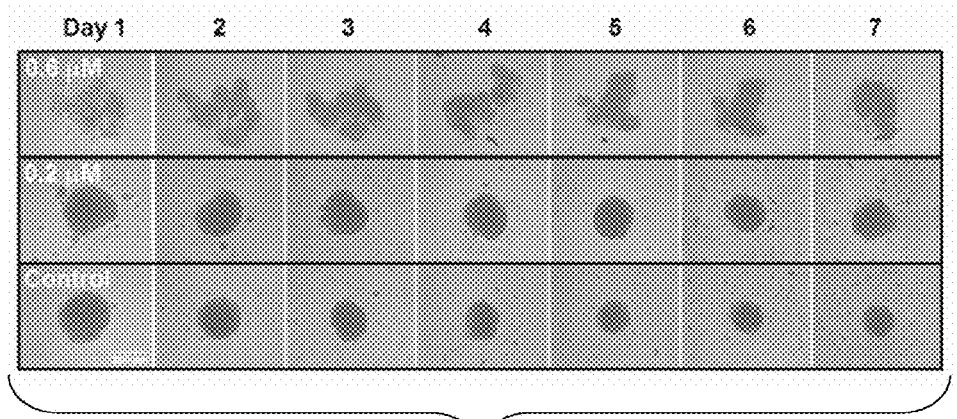
Figure 5C:
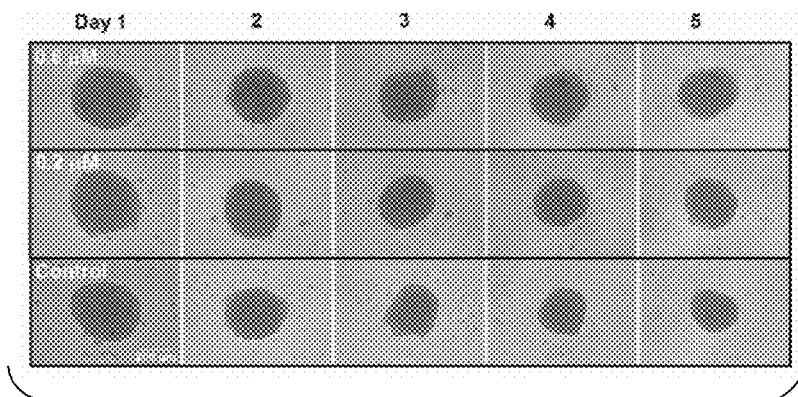
Figures 5D, 5E, 5F:
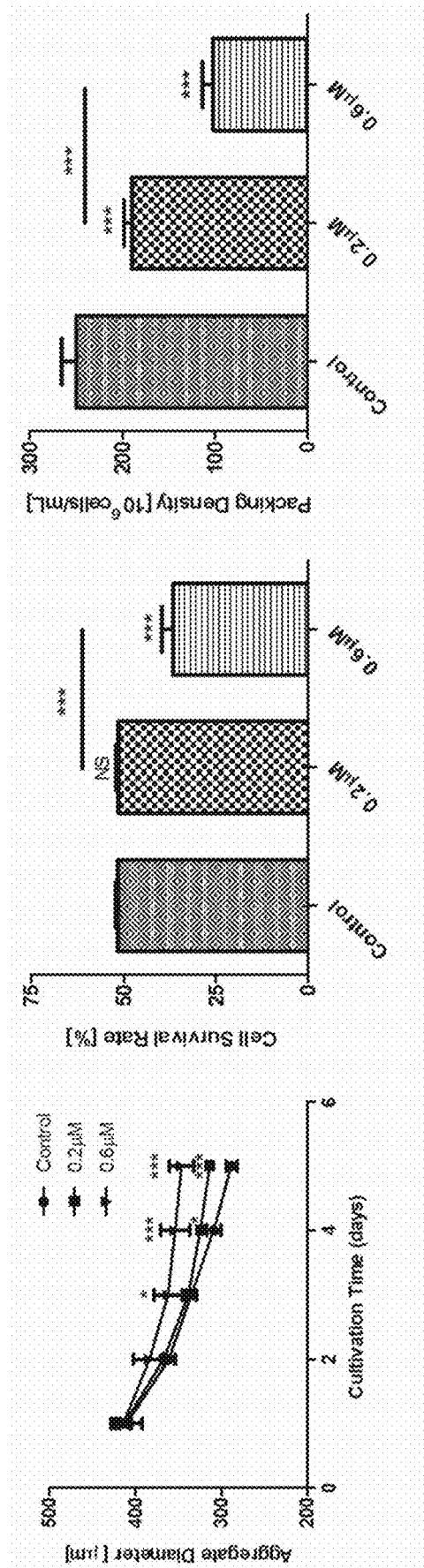

Example 1—Actin-Mediated Contractility Influences the Assembly of Multicellular hMSC Aggregates While the initial steps of aggregation require close contact and cell-cell adhesion via cadherin molecules, reorganization of actin cortical network is crucial in the establishment of a mature cell-cell contact (Amack and Manning 2012). To investigate the temporal effects of actin-mediated contractility in hMSC aggregate formation, hMSC cultures were treated with cytoD (1) in plastic culture for 2 days prior to cell detachment (e.g., 2D pretreatment) or (2) 12 hours after aggregate formation on ULA surfaces (i.e., 3D treatment). In 2D pretreatment, hMSC displayed dose-dependent response in which cytoD disrupted hMSC aggregation at concentration above 0.6 µM and prevented aggregate compaction at lower concentrations (FIGS. 5A and 5B). In 3D treatment, hMSC aggregates remained intact in cytoD concentration of 0.6 µM and exhibited dose-dependent reduction on compaction similar to those of 2D pretreatment group (FIGS. 5B-5D). In contrast, cytoD treatment prevented aggregate compaction but reduced cell viability, leading to significantly lower cell survival and packing density compared to control hMSC group at day 5 (FIGS. 5E and 5F).

Figure 6A:
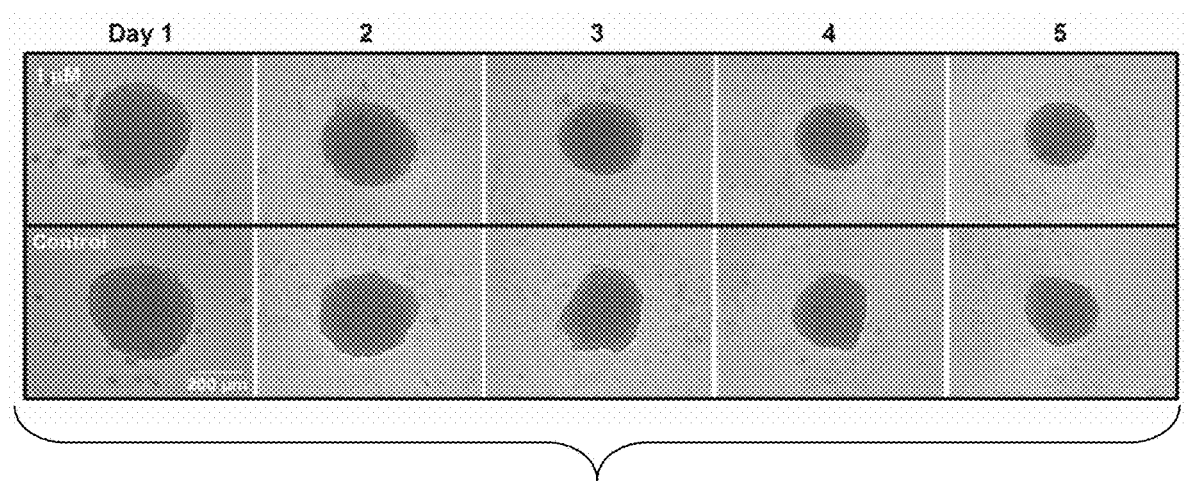
FIGS. 6A-6C. Aggregate treatment by nocodazole.
Figure 6B:
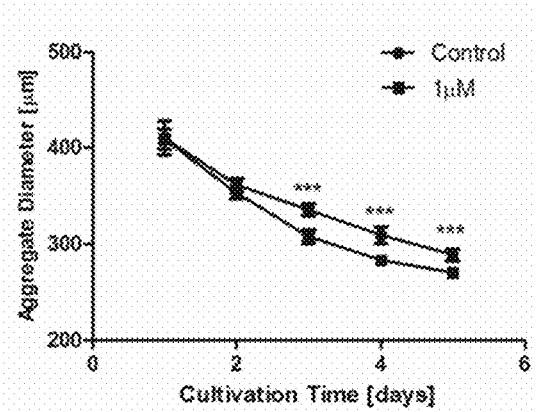
Figure 6C:
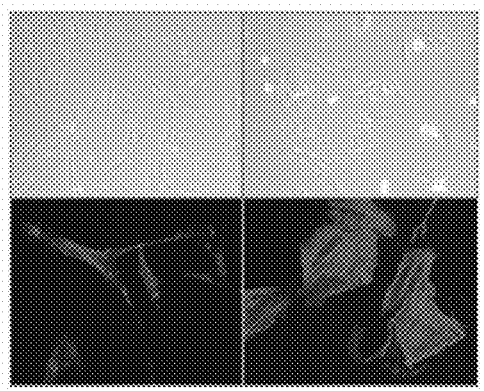
Figure 7A:
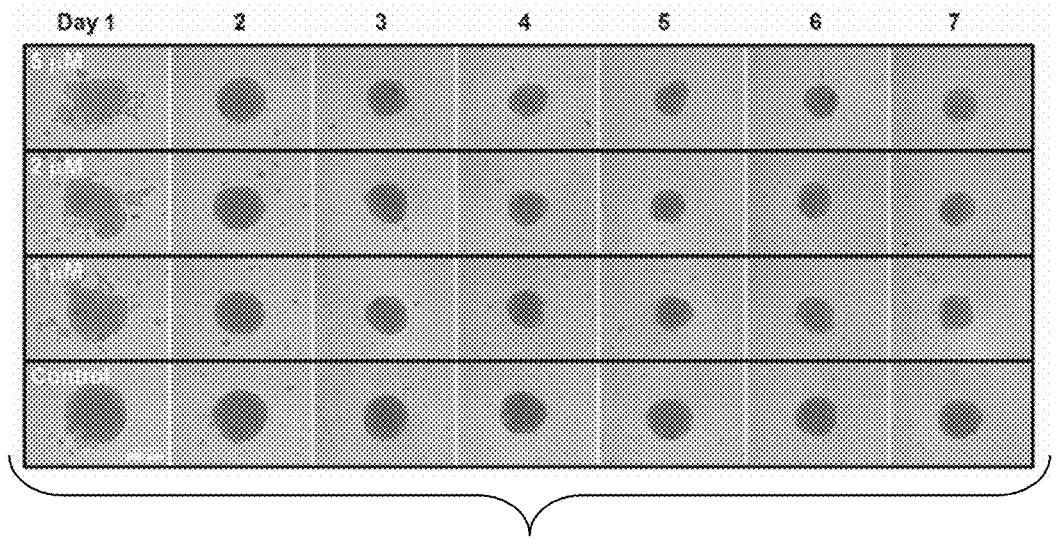
Figure 7B:
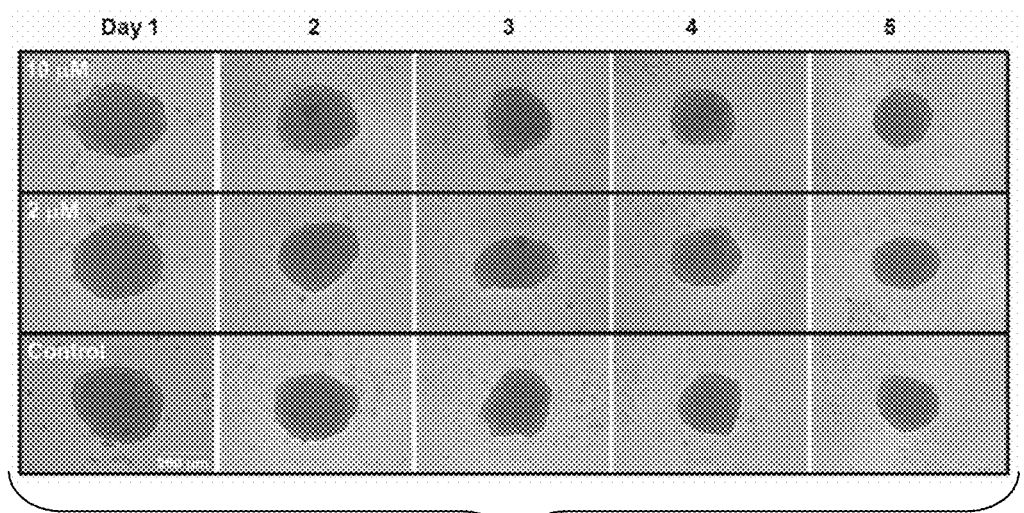
Figure 8A:
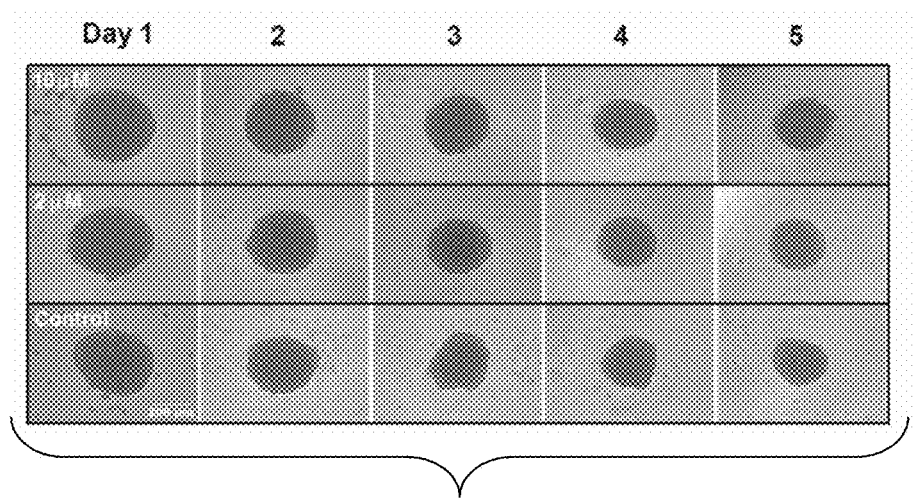
FIGS. 8A-8D. Aggregate treatment by Rock inhibitor Y-27632. Treatment by Y-27632 prevented aggregate compaction (FIG. 8A) with reduced decline in diameter of aggregates (FIG. 8B).
Figure 8B:
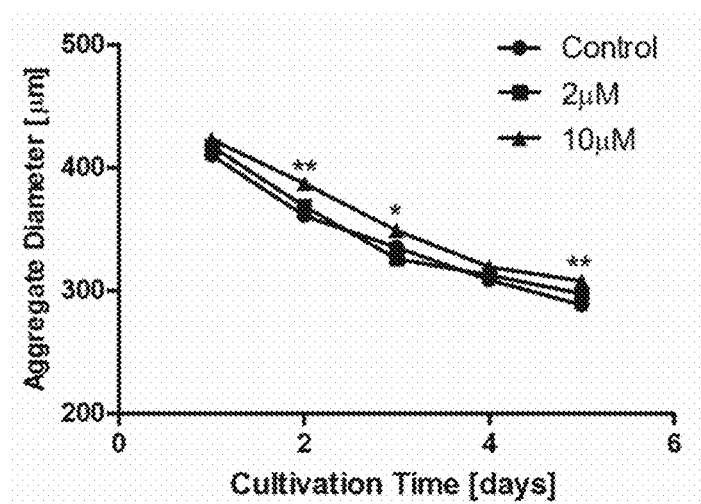
Figure 8C:
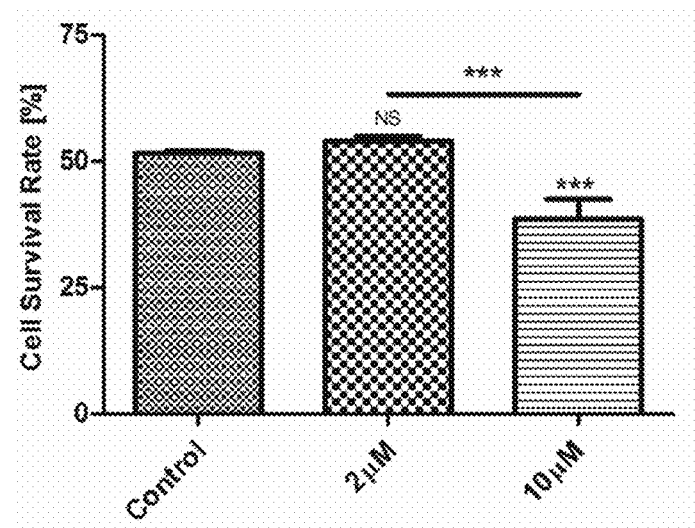
Figure 8D:
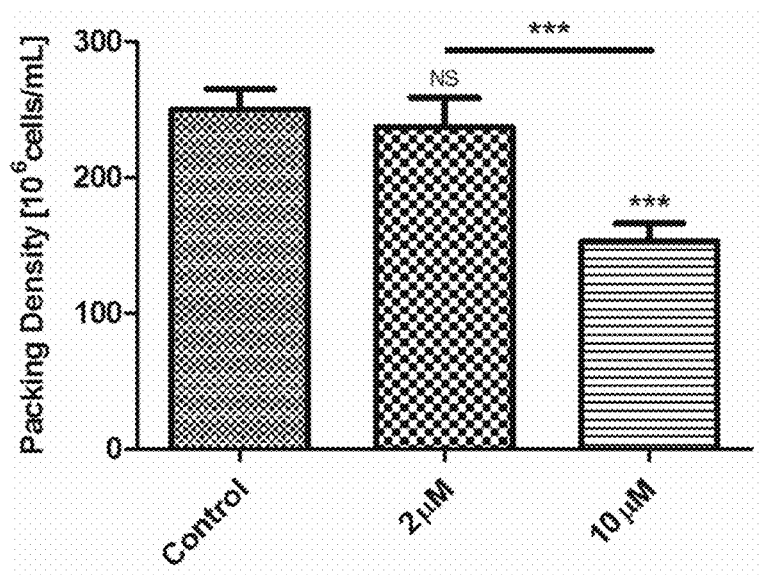

To investigate the role of microtubule in hMSC aggregates, the hMSC aggregates were treated by nocodazole, a chemical agent that interferes with the polymerization of microtubules. Despite the drastic changes of cell morphology on 2D surface, nocodozole-treated hMSC aggregates have comparable or higher compaction compared with the non-treated controls, suggesting microtubule is not the major force during aggregate compaction (FIGS. 6A-6C).

Example 2—Actin Mediates Aggregate Compaction but not Viability and Caspase Expression LPA is a naturally occurring bioactive phospholipid with multiple biological functions that include its ability to initiate cytoskeleton contraction by RhoA activation, promote cell survival and proliferation, and to enhance survival of hypoxia-challenged neonatal cardiomyocytes (Tigyi et al. 1994; Moolenaar 1995). LPA has also been identified as a novel survival factor and protects MSCs against hypoxia and serum deprivation-induced apoptosis (Chen et al. 2008a). Treatment of hMSC aggregates by LPA, however, has limited effects on aggregate compaction as well as viability at LPA concentration up to 10 µM (FIGS. 7A-7E).

The involvement of actin-myosin based contractility was investigated by treatment of aggregates with Y-27632, which inhibits the phosphorylation of Rho-associated kinase (ROCK) and prevents cell compaction (Chen et al. 2010). As expected, inhibition of ROCK kinase by 10 µM Y-27632 reduced aggregate compaction with a 6.7% increase in diameter by day 5 and a 38.7% decrease in cell packing density compared to the control aggregates (FIGS. 8A-8D). Despite significant reduction in aggregate compaction, cell viabilities in the Y-27632-treated aggregates were comparable or even less than those of control aggregates, suggesting reduced compaction by Y-27632 treatment failed to rescue hMSCs in the aggregates.

Figure 9A:
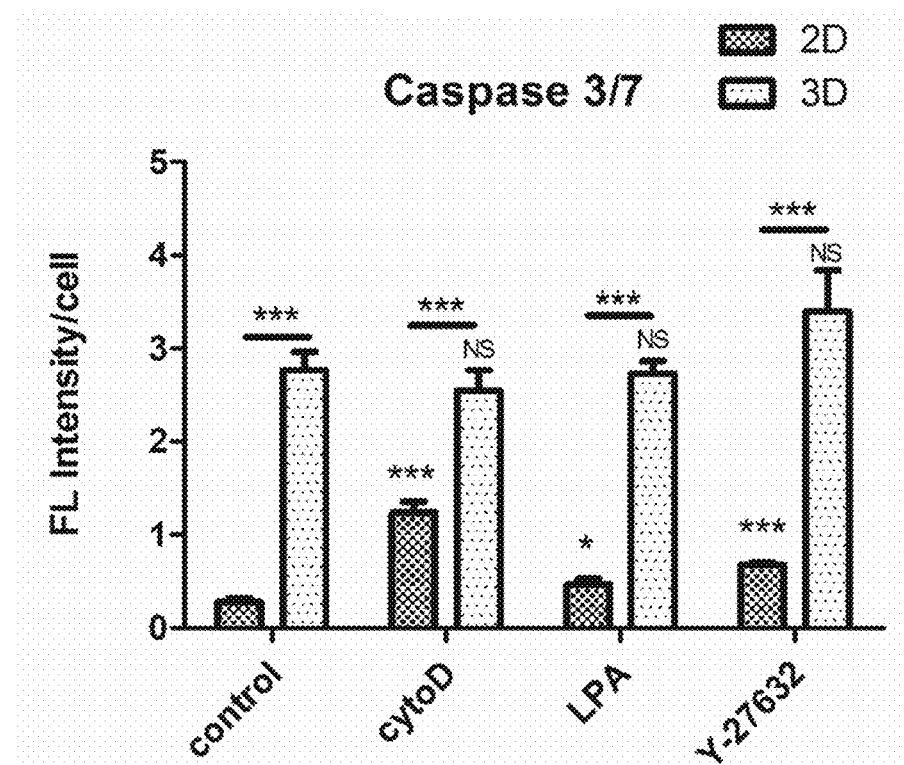
FIGS. 9A-9D. Caspase expression and inhibition.

Prior studies have reported increased apoptosis in hMSC aggregates (Bartosh et al. 2013; Kelm et al. 2012) but the origin of the stress signals remains to be resolved. Measurement of caspase 3/7 activity was used to quantify protein markers involved in late-stage apoptosis owing to its capacity to discriminate between apoptotic and necrotic cells (Chen et al. 2010). Compared to their counterparts in adherent 2D culture, formation of multi-cellular aggregates significantly increased caspase 3/7 activity for all treatment groups with the Y-27632-treated aggregates having the highest caspase 3/7 activity. CytoD treatment significantly increased caspase 3/7 activity in 2D adherent culture, whereas cytoD-treated aggregates had comparable apoptotic activity as hMSC control aggregates. Treatment by Y-27632 and LPA also increased caspase 3/7 activity in both 2D culture and 3D aggregates. These results suggest that prevention of aggregate compaction by actin modulators did not significantly reduce apoptosis, although the cytotoxic effects of the actin modulators may be a contributing factor (FIG. 9A).

Figure 9B:
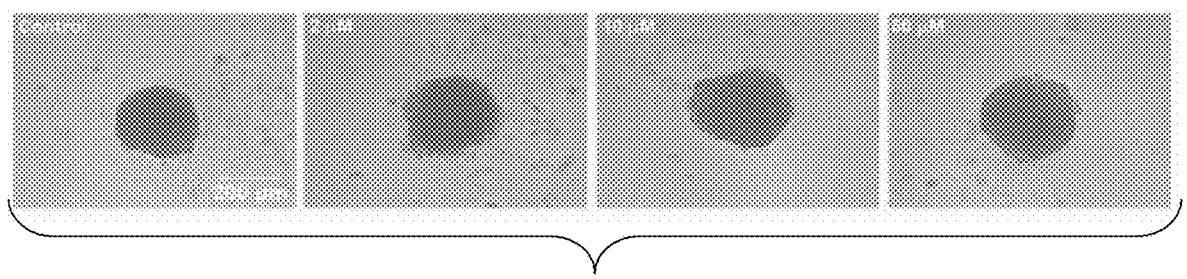
Figure 9D:
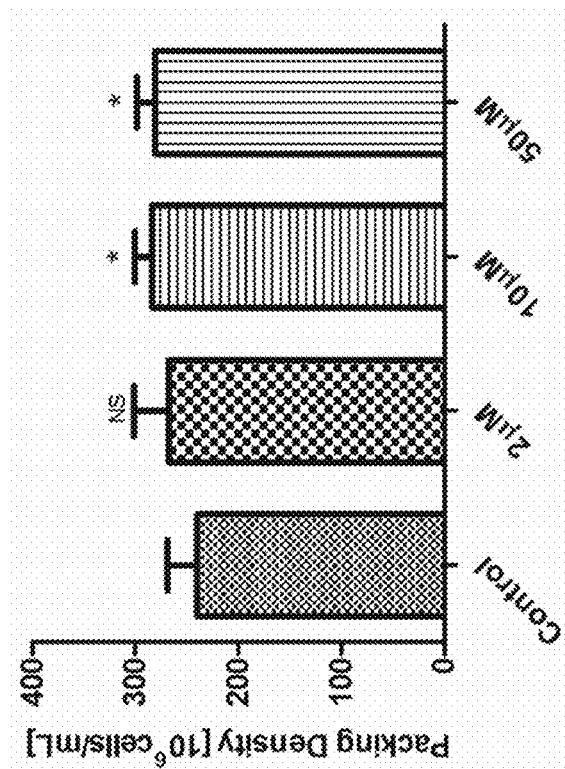
Figure 9C:
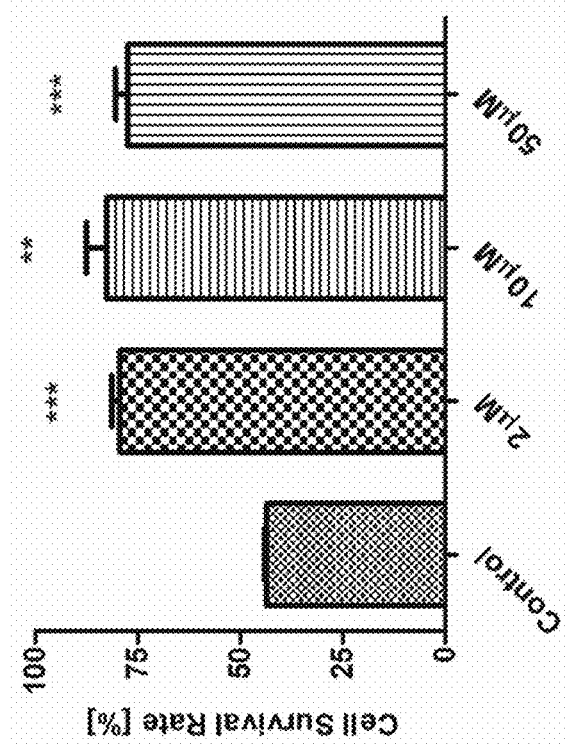

To determine the relation between apoptosis and aggregate compaction, hMSC aggregates were treated with Q-VD-OPh, a pan caspase inhibitor. After three days of culture, Q-VD-OPh-treated aggregates have reduced compaction and significantly increased cell viability compared to control, resulting in higher packing density (FIGS. 9B-9D). These results suggest cellular apoptosis is upstream of and partially contribute to aggregate compaction.

Figures 1, 10A:
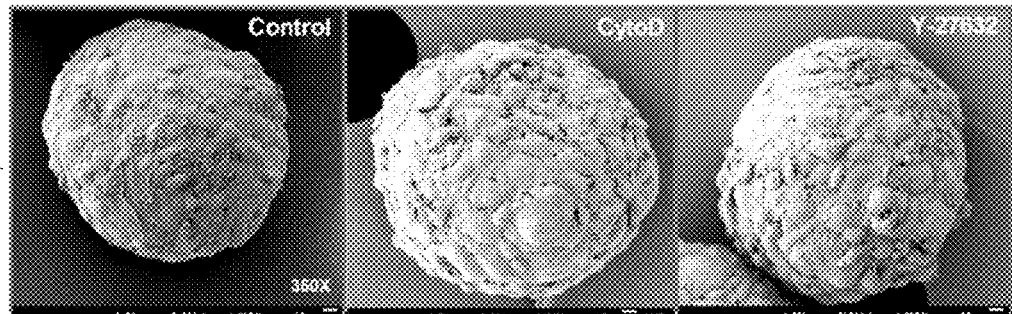
Figures 2, 10A:
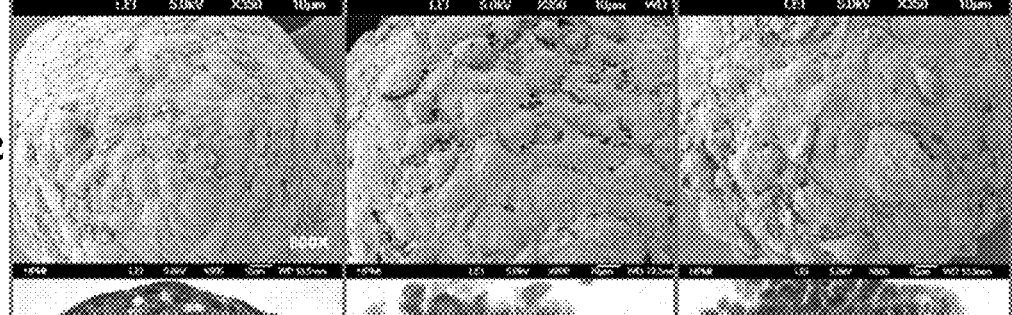
Figure 10B:
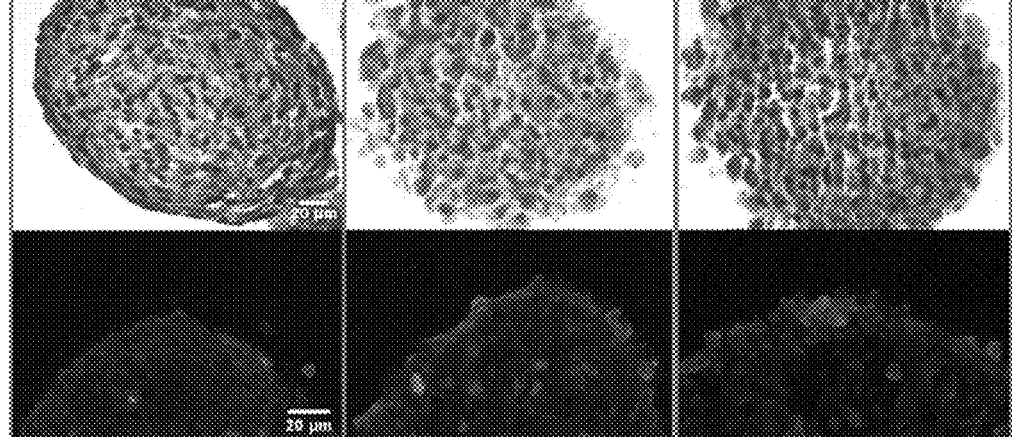
Figure 10C:

Example 3—Actin Mediates Aggregate Morphology, Interaction, and Spreading on Adherent Surfaces Disruption of actin significantly alters hMSC morphology in the aggregates. As shown in FIGS. 10A-1, 10A-2, 10B and 10C, cells in the hMSC aggregates were tightly packed and spread with limited interstitial space at the boundary of the aggregate. In contrast, cells in the cytoD- and Y-27632-treated aggregates were loosely packed and exhibited spherical morphology with abundant interstitial space as shown by SEM and histology (FIGS. 10A-1 and 10A-2). Histological sectioning also revealed contrasting morphology of hMSC in the interior of control and cytoD and Y-27632-treated aggregates. In the control aggregates, hMSCs are morphologically heterogeneous with spindle-shaped cells at the outer boundary and round and tightly packed cells in the interior, indicating morphological polarization. In the cytoD and Y-27632 treated aggregates, cells are loosely packed with no spreading at the boundary, indicating the absence of a mechanically polarized outer boundary (FIGS. 10B and 10C).

The tendency of cellular aggregates to spontaneously form spherical aggregates has been suggested to be analogous to the behavior of liquid drops that spontaneously acquire a spherical shape in suspension and fuse when placed in close contact to minimize surface tension (Gonzalez-Rodriguez et al. 2012). When placed in close contact, un-treated hMSC aggregates readily fused and spread on glass coverslip, so did the ones treated by LPA and nocodazole (FIGS. 11A and 11B). Y-27632-treated aggregates spread on glass coverslips but have reduced tendency to fuse. However, interrupting actin filaments by cytoD completely prevented aggregate spreading on glass coverslip and fusion of adjacent aggregates. Interestingly, after osteogenic induction, hMSC-OS aggregates maintained spherical shape on rigid glass coverslip and failed to fuse when in close contact. These results suggest that the viscoelastic behavior of hMSC aggregates is primarily mediated by actin.

Example 4—Functional Enhancement and Metabolic Alteration

Figure 12A:
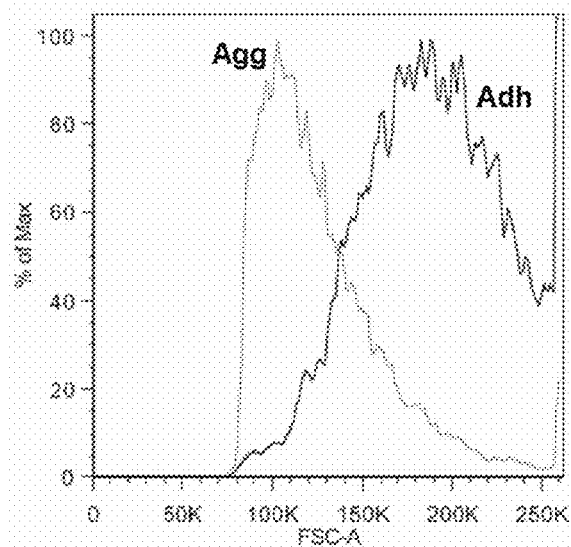
FIGS. 12A-12H. Cell size, morphology, migration, and hypoxia resistance of aggregate-derived hMSCs. hMSCs dissociated from aggregates are significantly smaller measured by flow cytometry (FIG. 12A) and light microscope (FIG. 12B) compared to 2D adherent control. When replated and cultured for 24 hours, aggregate-dissociated hMSCs are smaller compared to 2D adherent control (FIG. 12C). hMSCs dissociated from aggregates have significantly higher CXCR-4 expression measured by mean fluorescent intensity by flow cytometry (FIG. 12D) and higher migration toward SDF-1 in transwell assay (FIG. 12E).
Figure 12B:
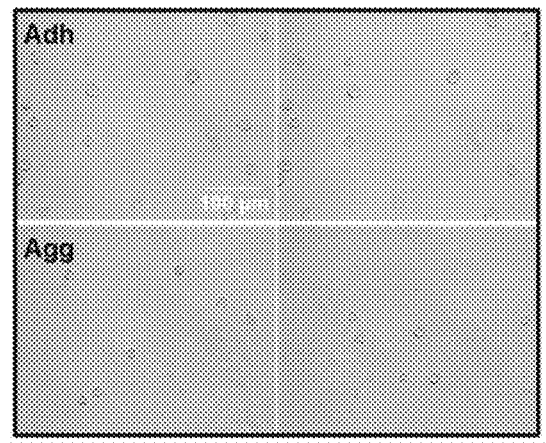
Figure 12C:
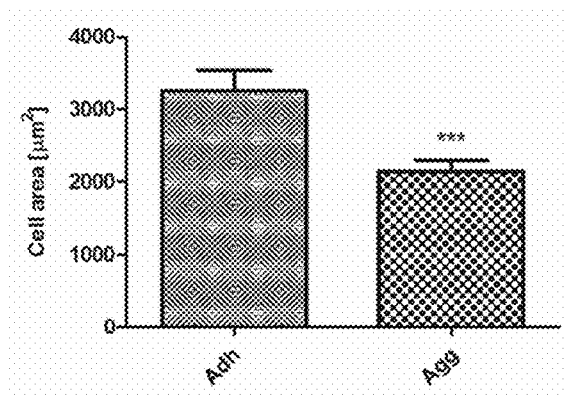
Figure 12D:
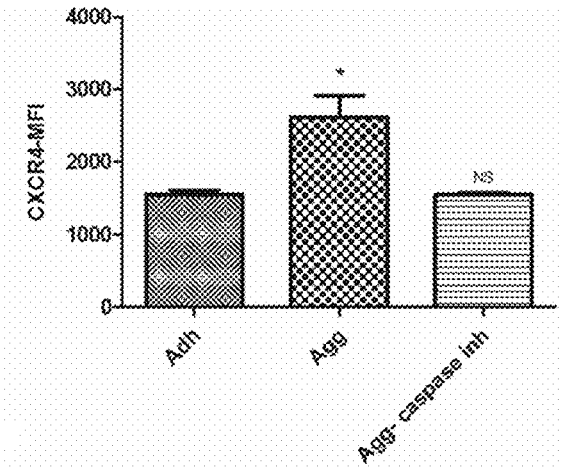
Figure 12E:
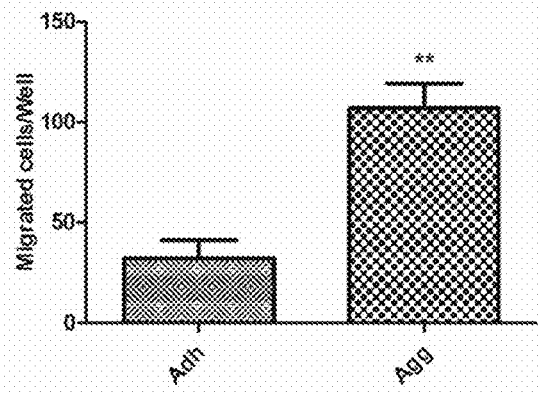
Figure 12F:
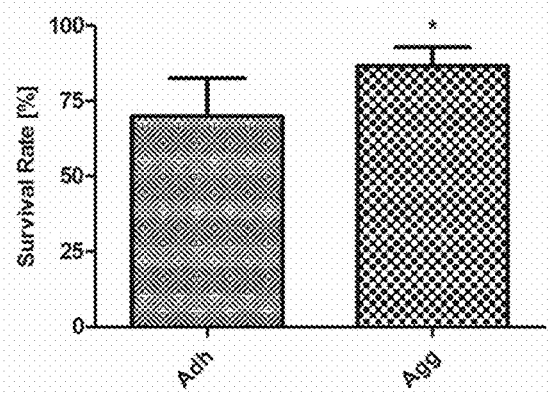

To evaluate the effects of 3D aggregation on hMSC properties, hMSC dissociated from the aggregates were characterized. As shown in FIGS. 12A and 12B, aggregate-derived hMSCs are significantly smaller than the 2D control with 36% reduction in diameter in suspension. After replating the aggregate-derived hMSCs on plastic culture dishes, they are also significantly smaller than their 2D counterparts (FIG. 12C). Aggregate-derived hMSCs also have significantly higher CXCR-4 expression and stronger migration ability toward SDF-1 indicated by transwell migration assay (FIGS. 12D and 12E). To further characterize hMSC's resistance to ischemic stress, aggregate-derived hMSCs and control from 2D adherent cultures were subject to in vitro ischemic (i.e., serum-free and 1% $O_2$) that mimics in vivo ischemic condition (FIG. 12F) (Kim and Ma 2013b). The results showed that aggregate-derived hMSCs have significantly higher survival under ischemic stress compared to their 2D counterparts. Collectively, the enhanced expression of CXCR-4, migration in response to SDF-1, resistance to ischemic stress, along with reduced cell size suggest the beneficial impact of 3D aggregation on hMSC properties in ischemic injuries.

Figure 12G:
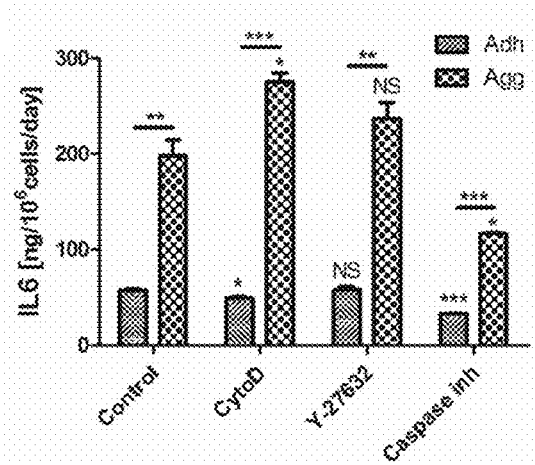
Figure 12H:
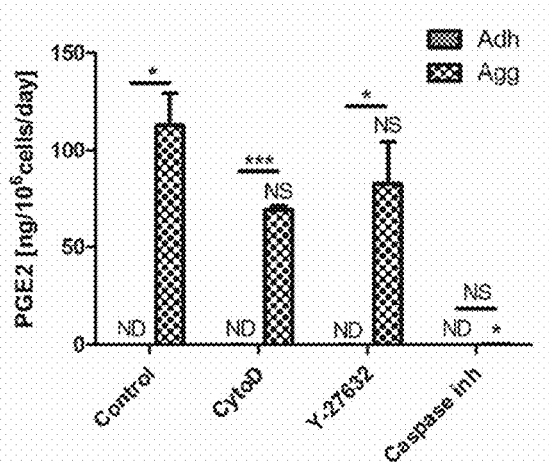

Elevated secretion of anti-inflammatory cytokine such as IL-6 and PGE-2 is thought to be due to hMSC stress response via caspase-mediated mechanism (Bartosh et al. 2013; Ylostalo et al. 2012). To investigate whether caspase inhibition attenuates hMSC secretory function, the aggregates were treated with Q-VD-OPh. As shown in FIGS. 12G and 12H, formation of 3D aggregates significantly upregulated the secretion of IL-6 and PGE-2 but this enhancement is attenuated to basal levels in the presence of Q-VD-OPh, suggesting the stress-induced functional activation in 3D aggregates. In addition, secretion of IL-6 and PGE-2 is independent from aggregate compaction because CytoD and Y-27632 treatment has limited effects on the levels of IL-6 and PGE-2.

Figures 13A, 13B:
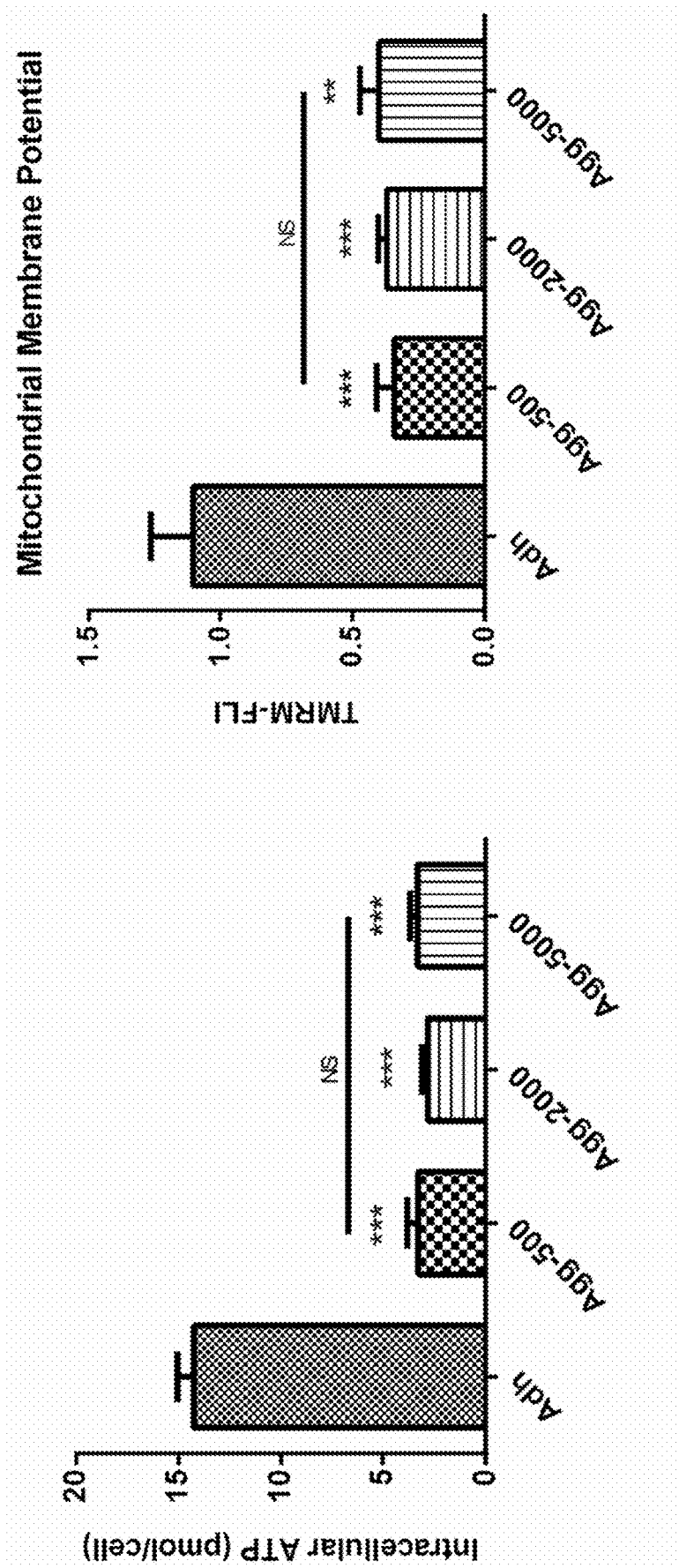
FIGS. 13A and 13B. Intracellular ATP and mitochondrial membrane potential.

To identify the source of stress signal and determine whether the impediment of oxygen and nutrients due to diffusion alters bioenergetics and results in apoptosis, cellular ATP contents/cell in aggregates of different sizes (e.g., 500, 2,000, and 5,000 cells/aggregates) were measured and compared to the adherent cells. All three aggregates have comparable ATP/cell contents but all are less than ⅓ of the adherent cells (FIG. 13A). The aggregate-size independent ATP/cell contents suggest diffusion limitation is not a primary factor for the reduced metabolic activity but aggregation altered hMSC energy metabolism. Indeed, accompanying the reduced ATP content, the aggregates have significantly reduced mitochondrial membrane potential (MMP) as measured by TMRM staining (FIG. 13B), suggesting increased mitochondrial depolarization as the major contributing factor to cellular apoptosis in 3D aggregates.

Example 5—Actin-Mediated Contractility Influences hMSC Aggregation, Compaction, and Fusion Isolated partially based on their plastic adherence, hMSCs are highly sensitive to biomechanical cues and substrate elasticity, which regulate hMSC lineage commitment and differentiation by modulating cytoskeletal tension and RhoA activation (Kilian et al. 2010; McBeath et al. 2004). The tension-mediated signaling is manifested in cytoskeletal contractility, in which reorganization of actin microfilaments plays a major role in hMSC realignment on topographical features and response to mechanical stimuli (Zhao et al. 2010; Engler et al. 2006). However, these studies have focused on the biomechanical cues on planar surfaces with primary impact on cell morphology and spreading (Kilian et al. 2010). In 3D setting, actin mediated contractility not only influences cell rounding, cell-cell contacts, and compaction, but also leads to biomechanical polarization that is known to play important roles in tissue organization and morphogenesis (Amack and Manning 2012). While studies have shown that 3D aggregation profoundly influence hMSC biological properties, the role of actin-mediated contractility in mediating the biomechanical properties of 3D aggregates such as fusion and spreading is yet to be fully understood.

Self-assembly of multicellular aggregates involves sequential steps of cell rounding, initial cell-cell contact, cadherin accumulation, and aggregate compaction, and requires reestablishment of the balance between surface and cortical tensions mediated by actin (Sart et al. 2014). According to the DAH by Steinberg (Steinberg 1962a; Steinberg 1962b), cadherins play a fundamental role in cell sorting and aggregation during tissue development and its perturbation interrupts limb development in vivo and influences hMSC multi-lineage differentiation in vitro (Oberlender and Tuan 1994; Shin et al. 2000; Yeh et al. 2012). However, this physics-based reasoning has been challenged by recent experimental evidence that adhesive molecules at the cortices of adhering cells not only mechanically couple the neighboring cells but also initiate local reorganization of actomyosin machinery that lead to "mechanical polarization" of initially identical cells at the boundary of a cell colony or aggregate (Amack and Manning 2012; Maitre et al. 2012). As a result, surface tension of aggregates is influenced by actomyosin-driven cell cortical contractility in multicellular aggregates (Krieg et al. 2008; Manning et al. 2010). Indeed, our results demonstrate that actomyosin contractility plays a crucial role in regulating hMSC aggregation and that disruption of actin filaments or inhibiting the phosphorylation of myosin light chain by Y-27632 prevented aggregate formation and reduced aggregate compaction in a dose-dependent manner.

Figure 14:
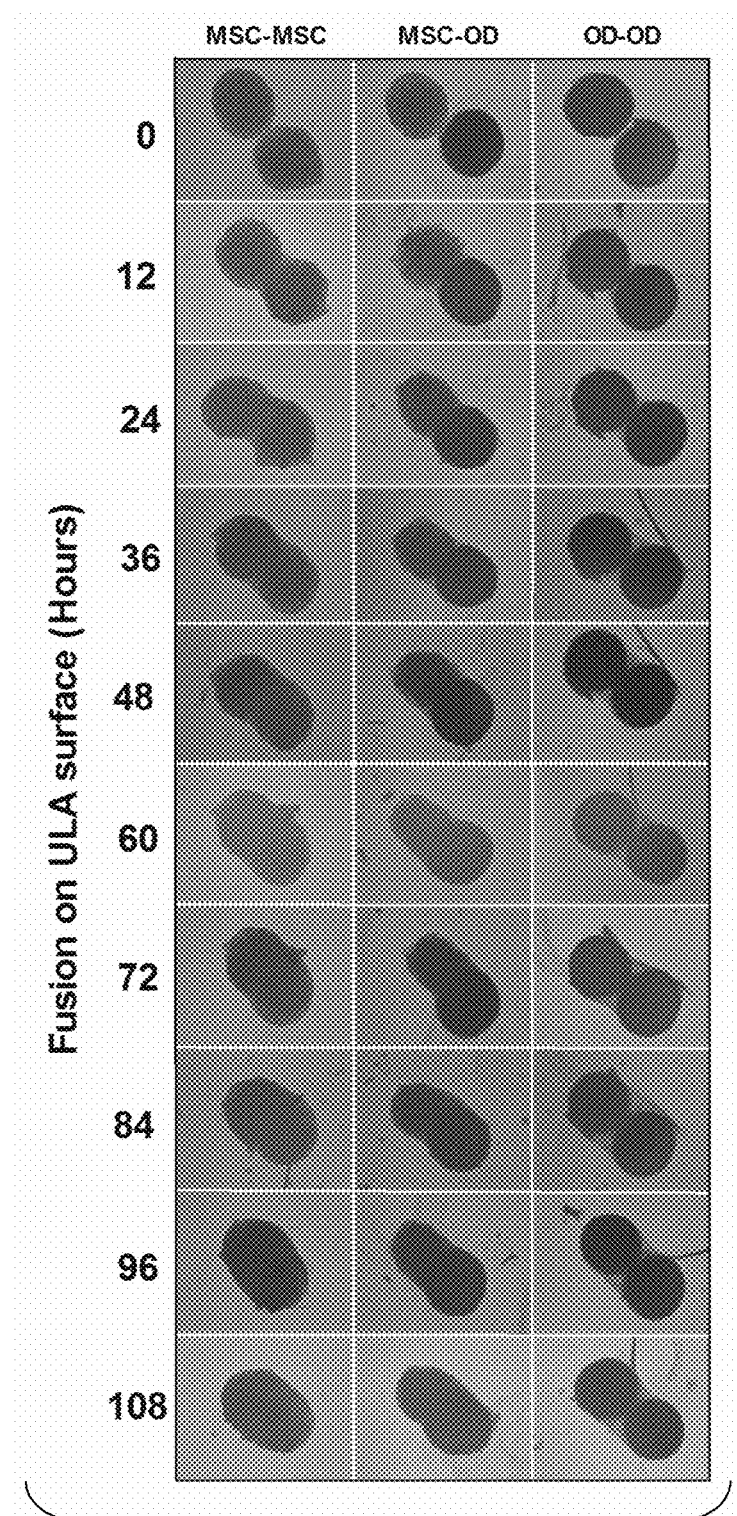
FIG. 14. Fusion of hMSC and osteogenic aggregates on ULA surface. Contacting hMSC aggregates fused within 24 hours, but OD aggregates did not fuse when placed in close contact on ULA surface after 108 hours. When placed in close contact, MSC aggregates enveloped the OD aggregates but no change in OD aggregates was observed after 48 hours. hMSC: hMSC aggregates treated with α-MEM for 7 days. OD: hMSC aggregates treated with osteogenic induction medium for 7 days.
Figure 15:
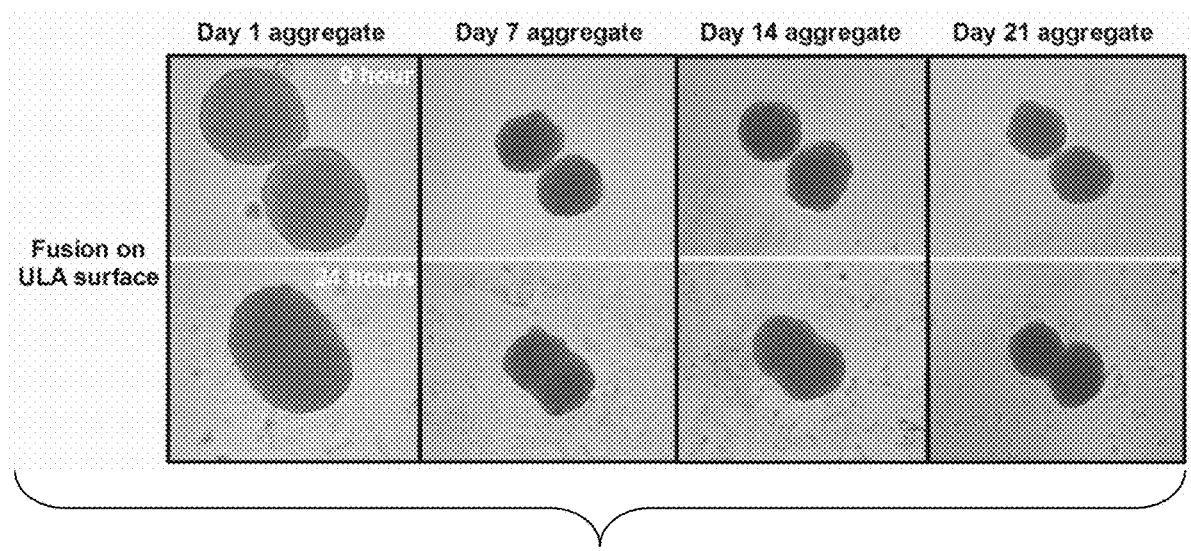
FIG. 15. Effects of culture time on fusion of hMSC aggregates on ULA surface. Extended culture time had little effects on hMSC fusion on ULA surface with only a slight delay after 21 days of culture.

Actin contractility also plays a major role in mediating aggregate fusion and spreading on rigid adherent surface in which disruption of actin by cytoD abolishes spreading and fusion of adjacent aggregates. In contrast, hMSC aggregates treated with nocodazole exhibited comparable contractility with control aggregates and readily spread on adherent surface and fuse with neighboring aggregates, confirming actomyosin-mediated contractility as the main force in aggregate compaction, spreading, and fusion. These results are in agreement with the tensegrity model of cell structure and support the notion that microtubules act as noncompressive structures of cytoskeleton to resist contractile tension of the actin and its inhibition has limited impact on aggregate compaction (Ingber 2003). It is of interest to note that the induction of osteogenic differentiation significantly reduced hMSC-OS aggregate spreading on adherent surfaces and fusion with neighboring aggregates. Osteogenic differentiation of hMSCs is accompanied by remarkable changes in cytoskeletal organization from a large number of thin, parallel actin microfilament bundles to a few thick actin filament bundles and corresponding changes in cell biomechanical properties (Rodriguez et al. 2004; Titushkin and Cho 2007). These changes are thought to be induced by osteoinductive components such as dexamethasone which is known to increase cell stiffness by influencing polymerization of actin microfilaments (Puig et al. 2009). Indeed, when placed in close contact, hMSC and OD aggregates displayed markedly different fusion properties with hMSC aggregates spread and enveloped OD aggregates (FIG. 14). On the other hand, hMSC aggregates maintained in growth media have comparable fusion properties even after extended culture up to 21 days (FIG. 15). Recent study suggests that chondrogenic induction by TGF-β leads to hMSC condensation and boundary formation (Bhumiratana et al. 2014). Together, these results suggest that hMSC phenotypic differentiation determines 3D aggregates' biomechanical properties and influences their self-assembly into functional units through cell fusion and sorting (Sart et al. 2014; Jakab et al. 2010).

Example 6—Caspase-Dependent Functional Activation

Caspase-dependent mechanism has been suggested as a major mechanism in functional activation associated with 3D hMSC aggregation but the origin of the apoptotic signal remains unclear. Aggregates of undifferentiated hMSCs experience considerable compaction and a marked decrease in relative amount of cytoplasm and cell volume and an increase in packing density (Bartosh et al. 2013). As such, aggregate compaction has been suggested as a contributing factor to self-activate caspase-dependent signaling and secretion of trophic factors (Bartosh et al. 2013; Kelm et al. 2012). However, reducing aggregate compaction by cytoD and Y-27632 treatments did not lead to increased cell viability nor reduced caspase 3/7 expression. While the actin modulators are pleiotropic and have cytotoxic effects on cell viability (Gourlay and Ayscough 2005), their limited reduction on aggregate caspase 3/7 expression in contrast to the significantly increased cell viability by caspase inhibitor (FIG. 9A) suggests an independent mediator for caspase activation in 3D aggregates.

Apart from biomechanical forces, impediment of oxygen transport and the resultant hypoxia region in the aggregates have been cited as a cellular stressor for the increase in caspase expression and subsequent functional activation (Bartosh et al. 2010). However, the comparable levels of size-independent ATP/cell in aggregates of different sizes provide direct evidence that oxygen diffusion is not a limiting factor in energy metabolism in the aggregates. In prior studies, immunostaining of the apoptotic activity in 3D hMSC aggregates revealed even distribution of apoptotic cells (Kelm et al. 2012) and that functional enhancement was also observed in aggregates below the threshold of oxygen transport (Zimmermann and Mcdevitt 2014; Ylostalo et al. 2012). In addition, oxygen is not limiting for electron transport in mitochondria until levels are extremely low; even at an $O_2$ concentration of 25 μM, electron transport is reduced only by 33% (Chandel et al. 1996). Thus, oxygen gradient is unlikely a direct contributing factor to the elevated apoptosis.

The comparable ATP/cell levels in aggregates of different sizes and their significant reduction compared to adherent cells suggest the changes in metabolic machinery following aggregation independent from substrate gradients due to diffusion. The drastic changes in cellular organization and creation of cellular and extracellular microenvironment during multicellular assembly of hMSCs 3D aggregates require effective reconfiguration of metabolic network for cell survival and function. hMSCs have been shown to use both glycolysis and OXPHO for ATP generation, exhibit metabolic flexibility for survival in an ischemic environment, and undergo coordinated changes of mitochondrial biogenesis during osteogenic differentiation (Chen et al. 2008b; Mylotte et al. 2008). The significant reduction of ATP/cell and the altered mitochondrial potential upon aggregation suggest changes in mitochondrial function that may directly contribute to the increased apoptosis. In contrast to mitochondrial transformation which usually occurs during cell differentiation or carcinogenesis, mitochondrial plasticity, known as mitoplasticity, plays an important role for the maintenance of cellular energy homeostasis and influences cell fate in response to energy imbalance due to accidental environmental changes in energy demand or supply (Jose et al. 2013). The drastic changes in actin dynamics during 3D aggregation may play a role in the altered mitochondria function in the aggregates as actin cytoskeleton influences mitochondrial organization, short-range movement, and function in mammalian cells (Sheng and Cai 2012; Quintero et al. 2009). One way that actin organization and dynamics in the cell influence mitochondrial network is by changes in the availability of polymerizable actin, thereby influencing morphology, connectivity, and ATP production of the mitochondrial network (Yu et al. 2010; Jayashankar and Rafelski 2014). In addition, the actin cytoskeleton is also an important physiological regulator of ROS release from mitochondria and that a reduction in actin dynamics leads to reduced mitochondria membrane potential, suggesting its key role in the upstream action of apoptosis pathways (Gourlay and Ayscough 2005). Apart from actin, mitochondrial properties in the aggregates may also be influenced and/or mitigated by mitogenic growth factors. Indeed, recent studies have shown that media composition and the presence of mitogenic factors in media significantly influence cell proliferation and secretory functions in the aggregates (Zimmermann and Mcdevitt 2014; Alimperti et al. 2014; Ylostalo et al. 2014). Thus, further study is warranted to decipher the exact contribution of actin-mediated biomechanical changes and metabolic adaption and apoptosis in hMSC aggregate's functional activation.

Example 7—Aggregation as a Preconditioning Strategy for hMSC Functional Activation Spontaneous multicellular aggregation appears to select cells that are small in size, have higher CXCR-4 expression, higher migration, and higher resistance to ischemic stress in vitro, suggesting the potential of aggregation as a preconditioning strategy for enhancing hMSC therapeutic properties (FIGS. 12A-12H). IL-6 is a cytokine that not only involved in inflammation but also has many regenerative and anti-inflammatory functions (Scheller et al. 2011), whereas PGE-2 is an important component of hMSC secretome that modulates both innate and adaptive immune responses (Aggarwal and Pittenger 2005). Our results confirmed prior observation and demonstrated that the enhanced secretion of IL-6 and PGE-2 is dependent on hMSC stress response and elevated apoptosis activity because the attenuation of apoptosis significantly reduced both PGE-2 and IL-6 secretions.

The results of present study demonstrate that actin-mediated contractility regulates aggregates biomechanical properties such as compaction, fusion, and spreading, and that 3D aggregation alters mitochondrial properties and induces cellular stress response and functional activation. The results also show that functional activation is regulated by caspase activation during aggregation but independent from actin-mediated compaction. Prior studies have shown that hMSC in vitro aging after extensive passaging altered mitochondrial morphology and decreased antioxidant capacities with reduced actin dynamic and migratory properties (Kasper et al. 2009; Geissler et al. 2012). Thus, the drastic changes in cytoskeleton during 3D aggregation may select a subset of hMSC that have dynamic actin turnover characteristic of MSC from young donor and enable them to effectively adapt during aggregate compaction. It is also possible that formation of 3D aggregates reverts hMSC back to an early phenotype as occurred when neural stem cells formed 3D neurospheres (Pastrana et al. 2011). Nevertheless, the results of current study support that notation that 3D aggregation significantly influences hMSC properties and can be used as a non-genetic preconditioning method to enhance the function and therapeutic outcome of culture-expanded hMSC in a wide range of diseases.

Figure 16A:
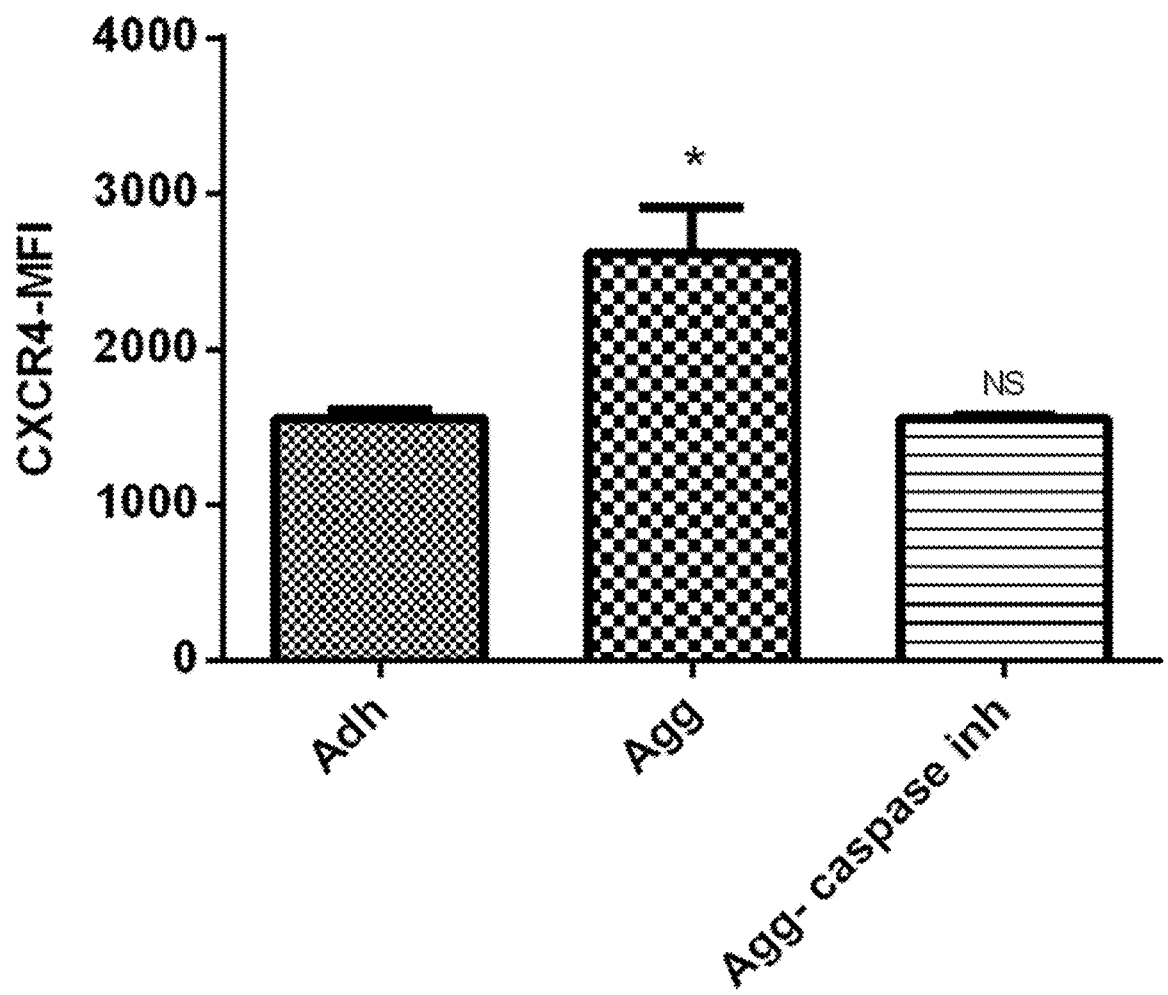
FIGS. 16A-16F.
Figure 16B:
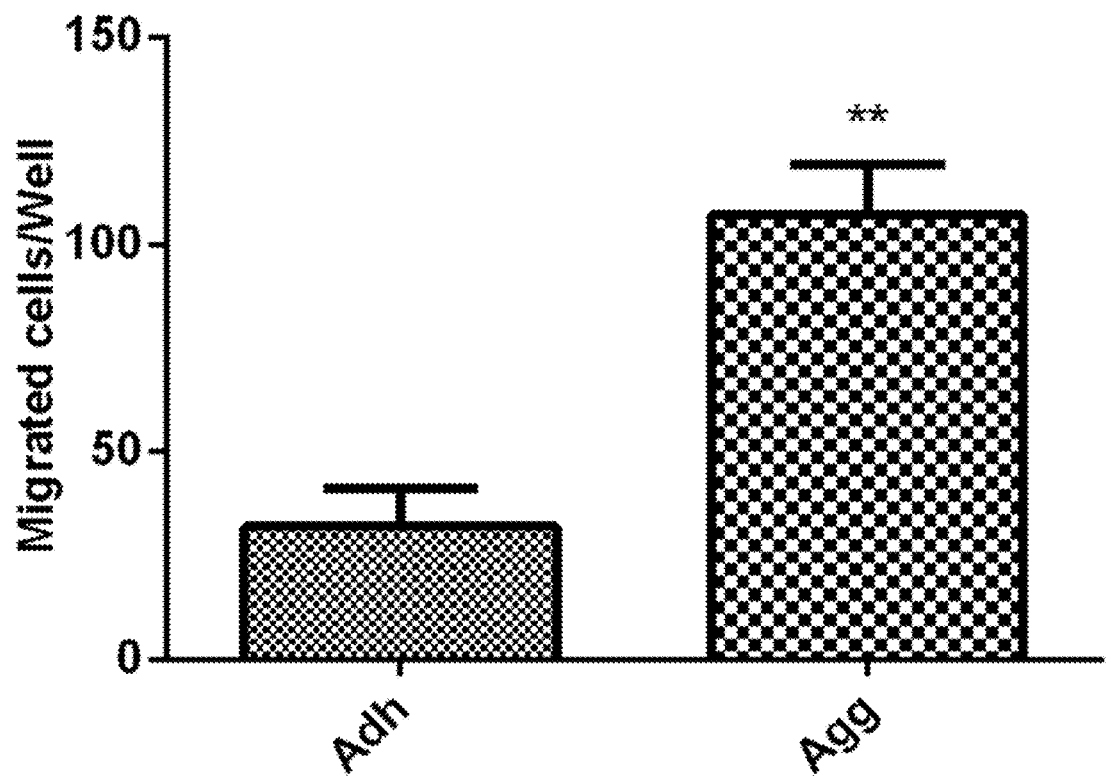
Figure 16C:
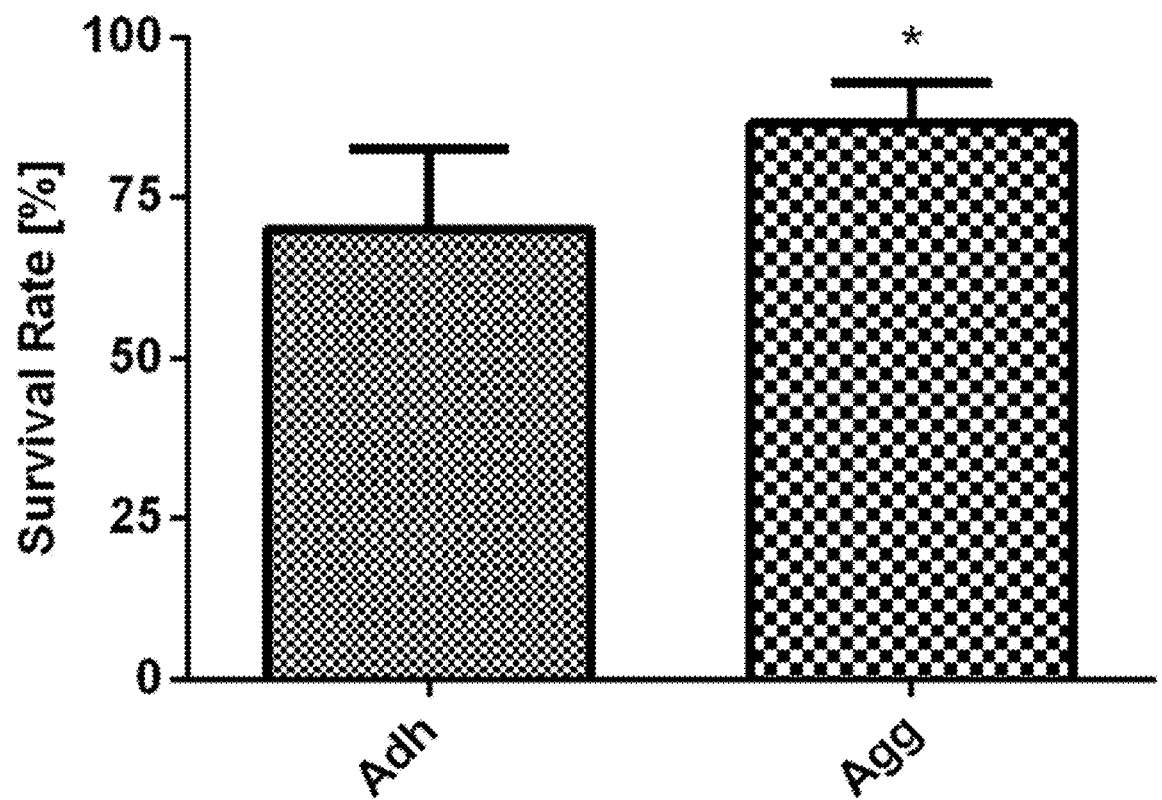
Figure 16D:
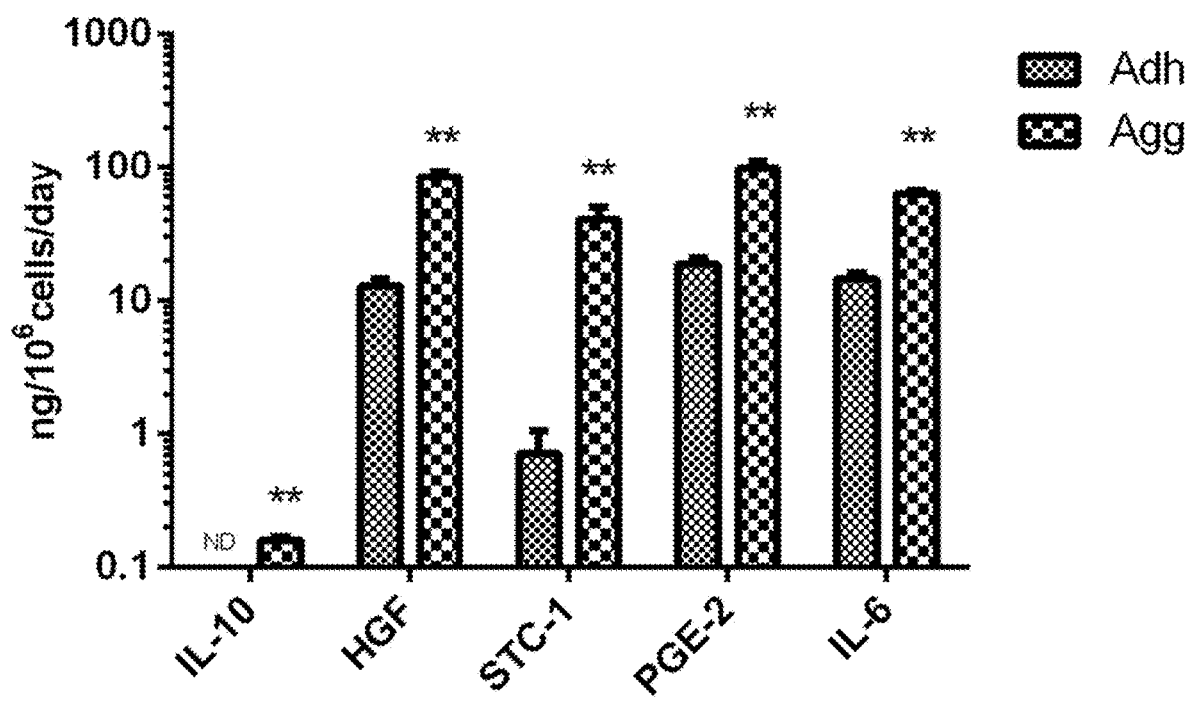
Figure 16E:
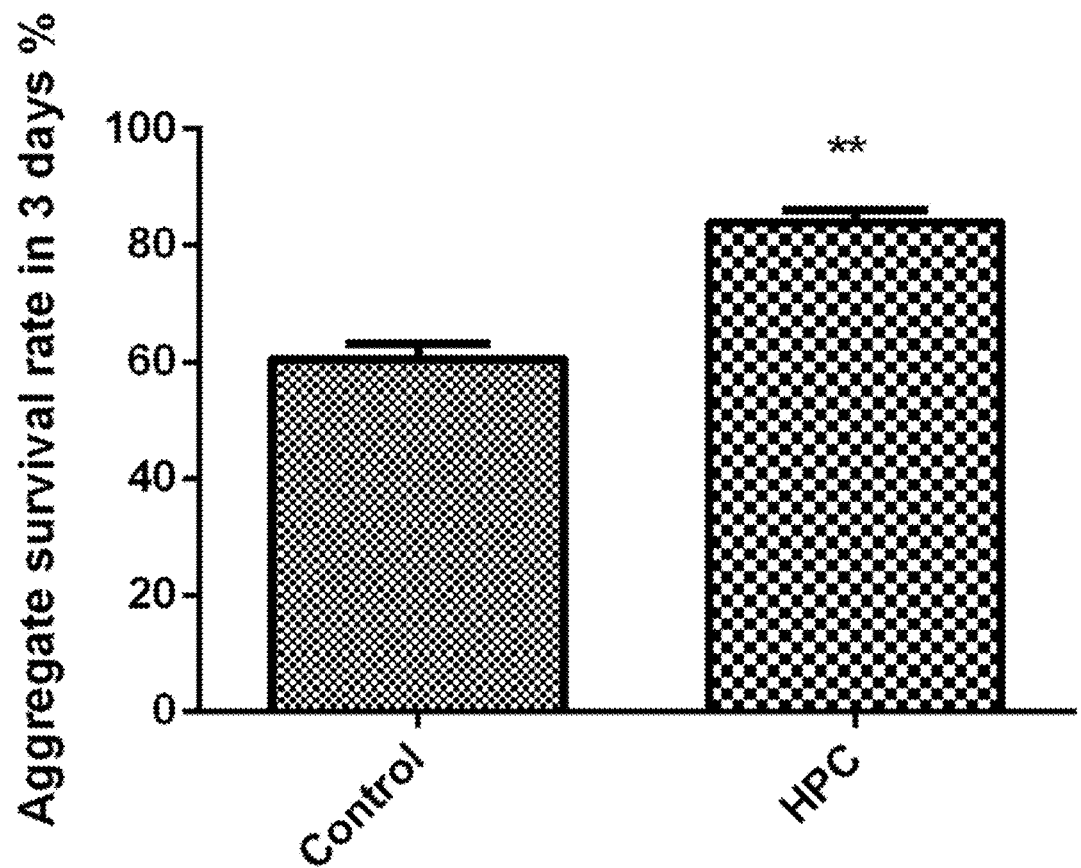
Figure 16F:
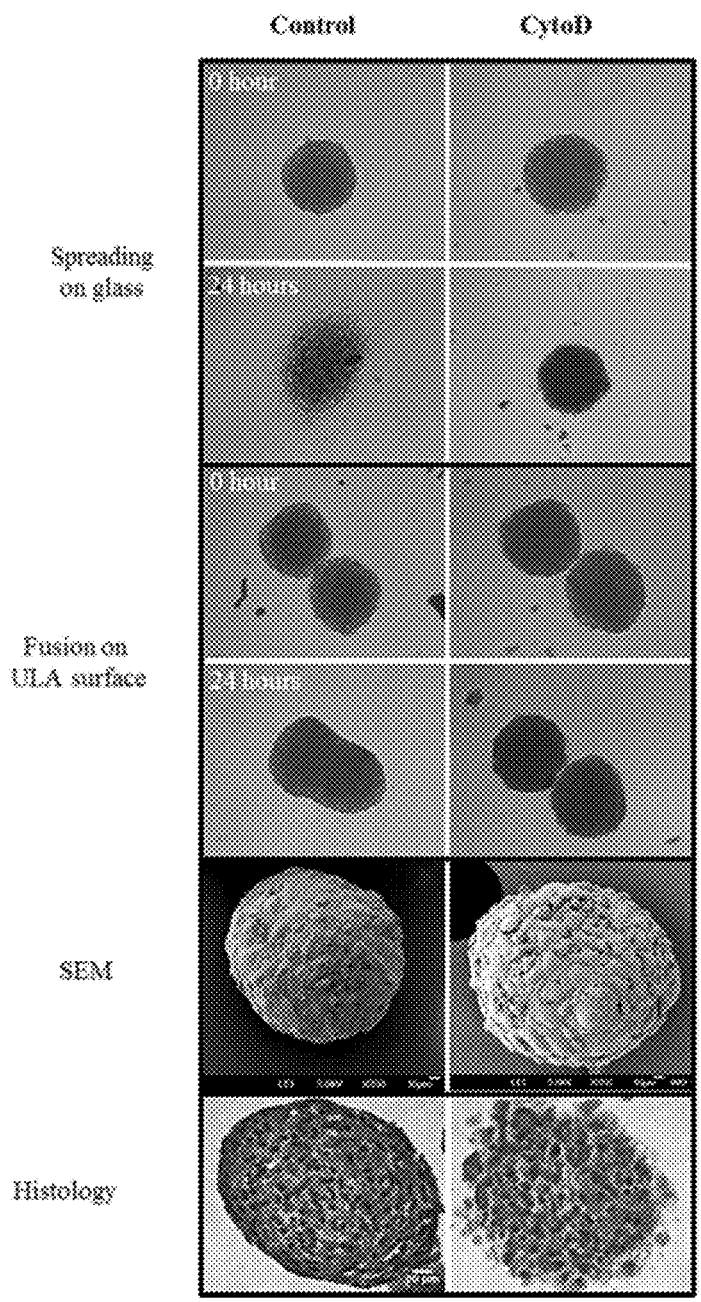

Example 8—Functional Activation of hBMSC by 3D Aggregation 5,000 hBMSCs seeded in 96-well ultralow attachment (ULA) plates spontaneously aggregated into 3D spheroids overnight. The hBMSC aggregates were able to fuse and maintained their ability to adhere to glass. cytochalasin D treatment of hBMSC aggregates abrogated their fusion and adhesion properties and disrupted the mechanically polarized outer layer as revealed by histology (FIG. 16F) suggesting that these properties are mediated by actin. hBMSC 3D aggregation significantly up-regulated CXCR-4 expression, migration towards SDF-1, and increased their resistance to in vitro ischemia (e.g., 2 hours in serum-free media under 2% $O_2$). hASC 3D aggregation enhanced expression of anti-inflammatory cytokines and growth factors (IL-10, HGF, STC-1, PGE-2, and IL-6). The hASC aggregates underwent compaction with a 40% reduction in cell number within 3 days, however hypoxia preconditioning (HPC) (i.e., expansion at 2% $O_2$ for 3 days before aggregation) significantly increased cell viability (FIGS. 16A-16E).

Example 9—Microcarrier Coating and Derivation of hBMSC Aggregates

Figure 17:
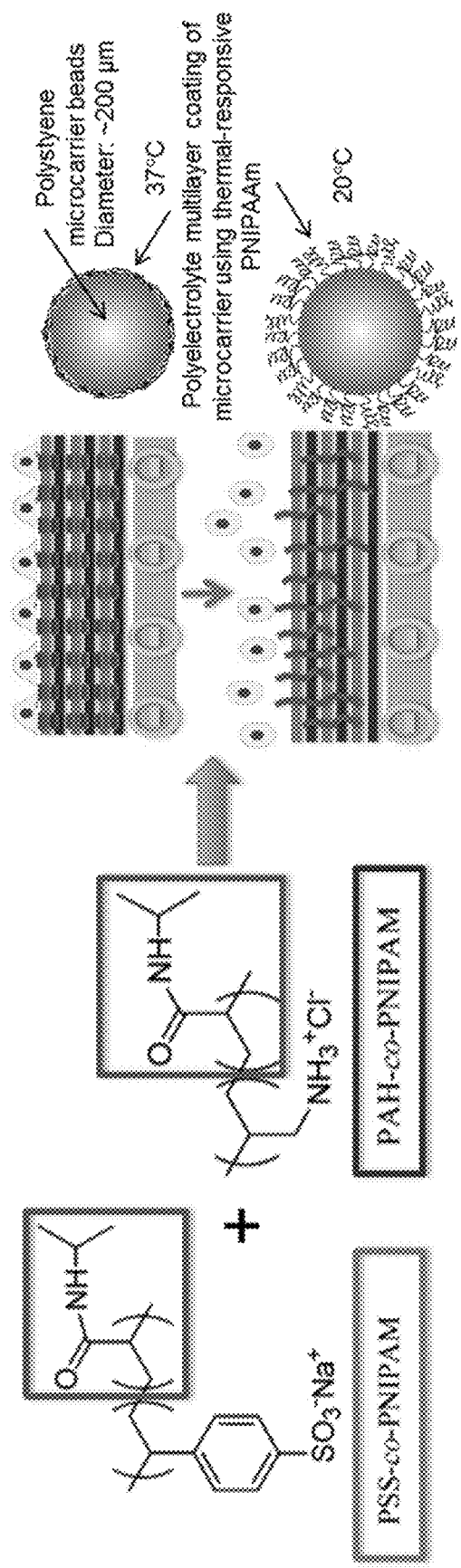
FIG. 17. Preparation of thermal responsive coating using PSS-co-PNIPAM and PAH-co-PNIPAM. Reducing temperature from 37° C. to 20° C. triggers pNIPAAm conformation change from collapsed to expanded state, triggering cell release.
Figure 18:
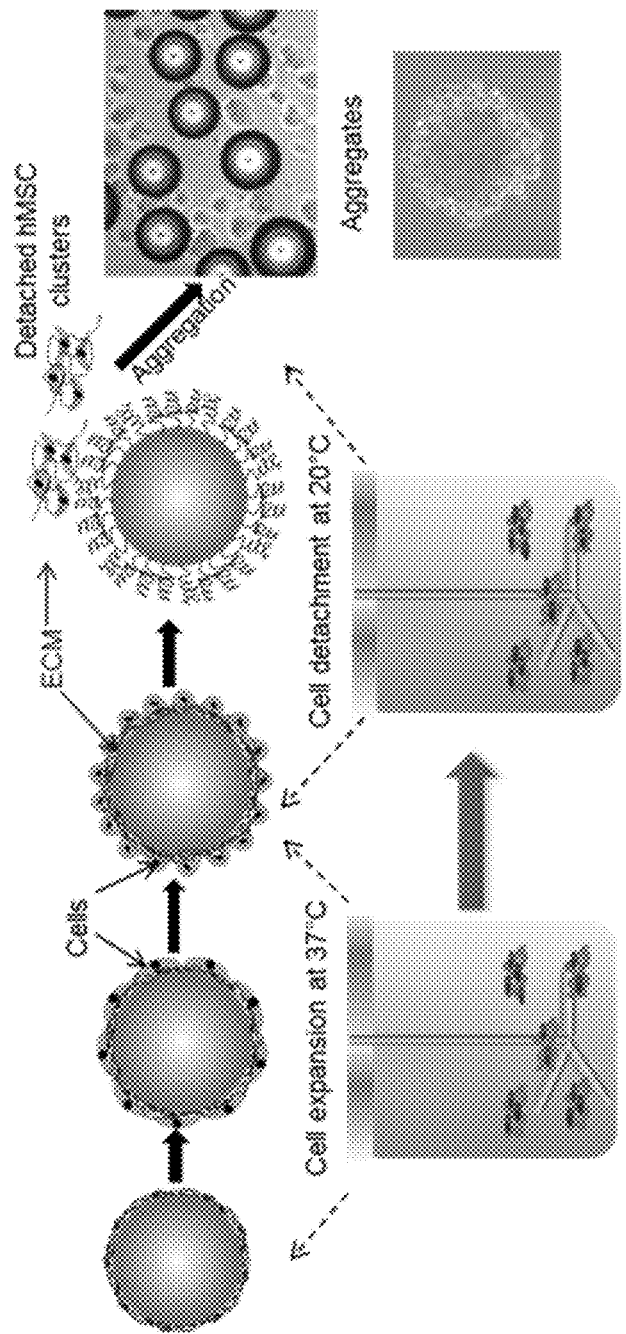
FIG. 18. After seeding, hBMSCs were expanded in the TRM bioreactor and expanded for 1 week at 37° C. At day 7, temperature is reduced to 20° C. to trigger release of hBMSC from microcarriers. The detached MSC clusters spontaneously coalesce and form 3D aggregates in suspension overnight.

FIG. 17 shows the procedure for coating of polystyrene microcarriers (SoloHill, Ann Arbor, Mich.) with poly(N-isopropylacrylamide) (PNIPAM)-based thermo-responsive film (Maitre et al. 2012). Alternating PSS-co-PNIPAM (Styrenesulfonate:Isopropylacrylamide=50:50 mol %) and PAH-co-PNIPAM (Allylamine:Isopropylacrylamide=50:50 mol %) were coated on the microcarriers, and the coating was confirmed by X-ray photoelectron spectroscopy and tested in the bioreactor. After seeding on the TRM, hBMSCs were expanded in the spinner flask for 7 days at 37° C. for a five-fold expansion and then moved to 20° C. to initiate cell detachment under agitation. After 2 hours at 20° C., hBMSC detachment is completed and the vessel returned to 37° C. for overnight culture to derive 3D aggregates. The results demonstrate the feasibility of integrated hBMSC expansion and derivation of 3D aggregates in a single bioreactor system (FIG. 18).

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

Aggarwal, S. and M. F. Pittenger, Human mesenchymal stem cells modulate allogeneic immune cell responses. Blood 105, 1815, 2005.
Alimperti, S., P. Lei, Y. Wen, J. Tian, A. M. Campbell, and S. T. Andreadis, Serum-free spheroid suspension culture maintains mesenchymal stem cell proliferation and differentiation potential. Biotechnology progress 30(4):974-983, 2014.
Amack, J. D. and M. L. Manning, Knowing the boundaries: extending the differential adhesion hypothesis in embryonic cell sorting. Science 338, 212, 2012.
Bara, J. J., R. G. Richards, M. Alini, and M. J. Stoddart, Concise review: Bone marrow-derived mesenchymal stem cells change phenotype following in vitro culture: Implications for basic research and the clinic. Stem Cells 32(7):1713-1723, 2014.
Baraniak, P. R., M. T. Cooke, R. Saeed, M. A. Kinney, K. M. Fridley, and T. C. McDevitt, Stiffening of human mesenchymal stem cell spheroid microenvironments induced by incorporation of gelatin microparticles. Journal of the Mechanical Behavior of Biomedical Materials 11, 63, 2012.
Bartosh, T. J., J. H. Ylostalo, A. Mohammadipoor, N. Bazhanov, K. Coble, K. Claypool, R. H. Lee, H. Choi, and D. J. Prockop, Aggregation of human mesenchymal stromal cells (MSCs) into 3D spheroids enhances their antiinflammatory properties. Proc Natl Acad Sci USA 107, 13724, 2010.
Bartosh, T. J., J. H. Ylostalo, N. Bazhanov, J. Kuhlman, and D. J. Prockop, Dynamic compaction of human mesenchymal stem/precursor cells into spheres self-activates caspase-dependent IL1 signaling to enhance secretion of modulators of inflammation and immunity (PGE2, TSG6, and STC1). Stem Cells 31, 2443, 2013.
Bhang, S. H., S. W. Cho, W. G. La, T. J. Lee, H. S. Yang, A. Y. Sun, S. H. Baek, J. W. Rhie, and B. S. Kim, Angiogenesis in ischemic tissue produced by spheroid grafting of human adipose-derived stromal cells. Biomaterials 32, 2734, 2011.
Bhumiratana, S., Eton, R. E., Oungoulian, S. R., Wan, L. Q., Ateshian, G. A., & Vunjak-Novakovic, G., Large, stratified, and mechanically functional human cartilage grown in vitro by mesenchymal condensation. Proceedings of the National Academy of Sciences, 111, 6940, 2014.
Chandel, N. S., G. R. Budinger, and P. T. Schumacker, Molecular oxygen modulates cytochrome c oxidase function. J Biol Chem 271, 18672, 1996.
Chavakis E, Dimmeler S. Homing of Progenitor Cells to Ischemic Tissues. *Antioxid Redox Sign.* 2011; 15:967-80.
Chen, J. H., A. R. Baydoun, R. X. Xu, L. Z. Deng, X. B. Liu, W. Q. Zhu, L. H. Shi, X. F. Cong, S. S. Hu, and X. Chen, Lysophosphatidic acid protects mesenchymal stem cells against hypoxia and serum deprivation-induced apoptosis. Stem Cells 26, 135, 2008a.
Chen, C. T., Y. R. V. Shih, T. K. Kuo, O. K. Lee, and Y. H. Wei, Coordinated changes of mitochondrial biogenesis and antioxidant enzymes during osteogenic differentiation of human mesenchymal stem cells. Stem Cells 26, 960, 2008b.
Chen, G. K., Z. G. Hou, D. R. Gulbranson, and J. A. Thomson, Actin-Myosin contractility is responsible for the reduced viability of dissociated human embryonic stem cells. Cell Stem Cell 7, 240, 2010.
Copland, I. B. and J. Galipeau, Death and inflammation following somatic cell transplantation. Seminars in Immunopathology 33, 535, 2011.
Dalby, M. J., N. Gadegaard, R. Tare, A. Andar, M. O. Riehle, P. Herzyk, C. D. W. Wilkinson, and R. O. C. Oreffo, The control of human mesenchymal cell differentiation using nanoscale symmetry and disorder. Nature Materials 6, 997, 2007.

dos Santos F F, Andrade P Z, da Silva C L, Cabral J M. Bioreactor design for clinical-grade expansion of stem cells. *Biotechnol J.* 2013; 8:644-54.

Elmore, S., Apoptosis: A review of programmed cell death. Toxicologic Pathology 35, 495, 2007.

Engler, A. J., S. Sen, H. L. Sweeney, and D. E. Discher, Matrix elasticity directs stem cell lineage specification. Cell 126, 677, 2006.

Fletcher, D. A. and D. Mullins, Cell mechanics and the cytoskeleton. Nature 463, 485, 2010.

Geissler, S., M. Textor, J. Kuhnisch, D. Konnig, O. Klein, A. Ode, T. Pfitzner, J. Adjaye, G. Kasper, and G. N. Duda, Functional comparison of chronological and in vitro aging: differential role of the cytoskeleton and mitochondria in mesenchymal stromal cells. Plos One 7(12): e52700, 2012.

Gonzalez-Rodriguez, D., K. Guevorkian, S. Douezan, and F. Brochard-Wyart, Soft Matter Models of Developing Tissues and Tumors. Science 338, 910, 2012.

Gourlay, C. W. and K. R. Ayscough, The actin cytoskeleton: a key regulator of apoptosis and ageing? Nat Rev Mol Cell Biol 6, 583, 2005.

Grayson W L, Ma T, Bunnell B. Human mesenchymal stem cells tissue development in 3D PET matrices. *Biotechnol Progr.* 2004; 20:905-12.

Grayson W L, Zhao F, Bunnell B, Ma T. Hypoxia enhances proliferation and tissue formation of human mesenchymal stem cells. *Biochem Bioph Res Comm.* 2007; 358:948-53.

Guo et al. (2014) Three-Dimensional Spheroid-Cultured Mesenchymal Stem Cells Devoid of Embolism Attenuate Brain Stroke Injury After Intra-Arterial Injection. Stem Cells and Development, DOI: DOI: 10.1089/scd.201 3.0338

Hildebrandt, C., H. Buth, and H. Thielecke, A scaffold-free in vitro model for osteogenesis of human mesenchymal stem cells. Tissue Cell 43, 91, 2011.

Ingber, D. E., Tensegrity I. Cell structure and hierarchical systems biology. J Cell Sci 116, 1157, 2003.

Ivascu, A. and M. Kubbies, Diversity of cell-mediated adhesions in breast cancer spheroids. International Journal of Oncology 31, 1403, 2007.

Jakab, K., Norotte, C., Marga, F., Murphy, K., Vunjak-Novakovic, G., & Forgacs, G., Tissue engineering by self-assembly and bio-printing of living cells. Biofabrication, 2, 022001, 2010.

Jayashankar, V. and S. M. Rafelski, Integrating mitochondrial organization and dynamics with cellular architecture. Current Opinion in Cell Biology 26, 34, 2014.

Jose, C., S. Melser, G. Benard, and R. Rossignol, Mitoplasticity: adaptation biology of the mitochondrion to the cellular redox state in physiology and carcinogenesis. Antioxidants & Redox Signaling 18, 808, 2013.

Kasper, G., L. Mao, S. Geissler, A. Draycheva, J. Trippens, J. Kuhnisch, M. Tschirschmann, K. Kaspar, C. Perka, G. N. Duda, and J. Klose, Insights into mesenchymal stem cell aging: involvement of antioxidant defense and actin cytoskeleton. Stem Cells 27, 1288, 2009.

Kelm, J. M., M. Breitbach, G. Fischer, B. Odermatt, I. Agarkova, B. K. Fleischmann, and S. P. Hoerstrup, 3D microtissue formation of undifferentiated bone marrow mesenchymal stem cells leads to elevated apoptosis. Tissue Eng Part A 18, 692, 2012.

Kilian, K. A., B. Bugarija, B. T. Lahn, and M. Mrksich, Geometric cues for directing the differentiation of mesenchymal stem cells. Proc Natl Acad Sci USA 107, 4872, 2010.

Kim, J. and T. Ma, Bioreactor strategy in bone tissue engineering: pre-culture and osteogenic differentiation under two flow configurations. Tissue Eng Part A 18(21-22):2354-2364, 2012.

Kim J. and T. Ma, Autocrine Fibroblast Growth Factor 2-Mediated Interactions between Human Mesenchymal Stem Cells and the Extracellular Matrix under Varying Oxygen Tension. *J Cell Biochem.* 114, 716-27, 2013a.

Kim, J. and T. Ma, Endogenous extracellular matrices enhance human mesenchymal stem cell aggregate formation and survival. Biotechnol Prog 29(2):441-451, 2013b.

Krieg, M., Y. Arboleda-Estudillo, P. H. Puech, J. Kafer, F. Graner, D. J. Muller, and C. P. Heisenberg, Tensile forces govern germ-layer organization in zebrafish. Nature Cell Biology 10, 429, 2008.

Lee E J, Park S J, Kang S K, Kim G H, Kang H J, Lee S W, et al. Spherical Bullet Formation via E-cadherin Promotes Therapeutic Potency of Mesenchymal Stem Cells Derived From Human Umbilical Cord Blood for Myocardial Infarction. *Molecular Therapy.* 2012; 20:1424-33.

Lee R H, Pulin A A, Seo M J, Kota D J, Ylostalo J, Larson B L, et al. Intravenous hMSCs Improve Myocardial Infarction in Mice because Cells Embolized in Lung Are Activated to Secrete the Anti-inflammatory Protein TSG-6. *Cell Stem Cell.* 2009; 5:54-63.

Li W Y, Choi Y J, Lee P H, Huh K, Kang Y M, Kim H S, et al. Mesenchymal Stem Cells for Ischemic Stroke: Changes in Effects After Ex Vivo Culturing. *Cell Transplant.* 2008; 17:1045-59.

Liao T, Moussallem M D, Kim J, Schlenoffd J B, Ma T. N-Isopropylacrylamide-Based Thermoresponsive Polyelectrolyte Multilayer Films for Human Mesenchymal Stem Cell Expansion. *Biotechnol. Prog.,* 2010, 26, 1705-1713.

Lin, R. Z. and H. Y. Chang, Recent advances in three-dimensional multicellular spheroid culture for biomedical research. Biotechnology Journal 3, 1172, 2008.

Lin, R. Z., L. F. Chou, C. C. M. Chien, and H. Y. Chang, Dynamic analysis of hepatoma spheroid formation: roles of E-cadherin and beta 1-integrin. Cell and Tissue Research 324, 411, 2006.

Liu H, Xue W, Ge G, Luo X, Li Y, Xiang H, et al. Hypoxic preconditioning advances CXCR4 and CXCR7 expression by activating HIF-1alpha in MSCs. *Biochem Biophys Res Commun.* 2010; 401:509-15.

Maitre, J. L., H. Berthoumieux, S. F. G. Krens, G. Salbreux, F. Julicher, E. Paluch, and C. P. Heisenberg, Adhesion functions in cell sorting by mechanically coupling the cortices of adhering cells. Science 338, 253, 2012.

Manning, M. L., R. A. Foty, M. S. Steinberg, and E. M. Schoetz, Coaction of intercellular adhesion and cortical tension specifies tissue surface tension. Proc Natl Acad Sci USA 107, 12517, 2010.

McBeath, R., D. M. Pirone, C. M. Nelson, K. Bhadriraju, and C. S. Chen, Cell shape, cytoskeletal tension, and RhoA regulate stem cell lineage commitment. Developmental Cell 6, 483, 2004.

Moolenaar, W. H., Lysophosphatidic acid, a multifunctional phospholipid messenger. Journal of Biological Chemistry 270, 12949, 1995.

Moussallem M D, Olenych S G, Scott S L, Keller T C, 3rd, Schlenoff J B. Smooth muscle cell phenotype modulation and contraction on native and cross-linked polyelectrolyte multilayers. *Biomacromolecules.* 2009; 10:3062-8.

Munoz, N., J. Kim, Y. Liu, T. M. Logan, and T. Ma, Gas chromatography-mass spectrometry analysis of human mesenchymal stem cell metabolism during proliferation and osteogenic differentiation under different oxygen tensions. Journal of Biotechnology 169, 95, 2014.

Mylotte, L. A., A. M. Duffy, M. Murphy, T. O'Brien, A. Samali, F. Barry, and E. Szegezdi, Metabolic flexibility permits mesenchymal stem cell survival in an ischemic environment. Stem Cells 26, 1325, 2008.

Nelson, C. M., R. P. Jean, J. L. Tan, W. F. Liu, N.J. Sniadecki, A. A. Spector, and C. S. Chen, Emergent patterns of growth controlled by multicellular form and mechanics. Proc Natl Acad Sci USA 102, 11594, 2005.

Numasawa Y, Kimura T, Miyoshi S, Nishiyama N, Hida N, Tsuji H, et al. Treatment of human mesenchymal stem cells with angiotensin receptor blocker improved efficiency of cardiomyogenic transdifferentiation and improved cardiac function via angiogenesis. *Stem Cells.* 2011; 29:1405-14.

Oberlender, S. A. and R. S. Tuan, Expression and functional involvement of N-cadherin in embryonic limb chondrogenesis. Development 120, 177, 1994.

Olenych S G, Moussallem M D, Salloum D S, Schlenoff J B, Keller T C. Fibronectin and cell attachment to cell and protein resistant polyelectrolyte surfaces. Biomacromolecules. 2005; 6:3252-8.

Parekkadan B, Milwid J M. Mesenchymal Stem Cells as Therapeutics. *Annu Rev Biomed Eng.* 2010; 12:87-117.

Pastrana, E., V. Silva-Vargas, and F. Doetsch, Eyes wide open: a critical review of sphere-formation as an assay for stem cells. Cell Stem Cell 8, 486, 2011.

Potapova, I. A., P. R. Brink, I. S. Cohen, and S. V. Doronin, Culturing of human mesenchymal stem cells as three-dimensional aggregates induces functional expression of CXCR4 that regulates adhesion to endothelial cells. J Biol Chem 283, 13100, 2008.

Prockop, D. J., D. J. Kota, N. Bazhanov, and R. L. Reger, Evolving paradigms for repair of tissues by adult stem/progenitor cells (MSCs). J Cell Mol Med 14, 2190, 2010.

Puig, F., N. Gavara, R. Sunyer, A. Carreras, R. Farre, and D. Navajas, Stiffening and contraction induced by dexamethasone in alveolar epithelial cells. Experimental Mechanics 49, 47, 2009.

Quintero, O. A., M. M. DiVito, R. C. Adikes, M. B. Kortan, L. B. Case, A. J. Lier, N. S. Panaretos, S. Q. Slater, M. Rengarajan, M. Feliu, and R. E. Cheney, Human Myo19 Is a Novel myosin that associates with mitochondria. Current Biology 19, 2008, 2009.

Rivron, N. C., E. J. Vrij, J. Rouwkema, S. Le Gac, A. van den Berg, R. K. Truckenmuller, and C. A. van Blitterswijk, Tissue deformation spatially modulates VEGF signaling and angiogenesis. Proc Natl Acad Sci USA 109, 6886, 2012.

Rodriguez, J. P., M. Gonzalez, S. Rios, and V. Cambiazo, Cytoskeletal organization of human mesenchymal stem cells (MSC) changes during their osteogenic differentiation. Journal of Cellular Biochemistry 93, 721, 2004.

Rombouts W J C, Ploemacher R E. Primary murine MSC show highly efficient homing to the bone marrow but lose homing ability following culture. *Leukemia.* 2003; 17:160-70.

Russell, K. C., D. G. Phinney, M. R. Lacey, B. L. Barrilleaux, K. E. Meyertholen, and K. C. O'Connor, In vitro high-capacity assay to quantify the clonal heterogeneity in trilineage potential of mesenchymal stem cells reveals a complex hierarchy of lineage commitment. Stem Cells 28, 788, 2010.

Sart, S., A. C. Tsai, Y. Li, and T. Ma, Three-dimensional aggregates of mesenchymal stem cells: cellular mechanisms, biological properties, and applications. Tissue Engineering Part B, Reviews, 20(5):365-380, 2014.

Scheller, J., A. Chalaris, D. Schmidt-Arras, and S. Rose-John, The pro- and anti-inflammatory properties of the cytokine interleukin-6. Biochim Biophys Acta 1813, 878, 2011.

Sepulveda, J. C., M. Tome, M. E. Fernandez, M. Delgado, J. Campisi, A. Bernad, and M. A. Gonzalez, Cell senescence abrogates the therapeutic potential of human mesenchymal stem cells in the lethal endotoxemia model. Stem Cells 32(7):1865-1877, 2014.

Sharma S, Raju R, Sui S G, Hu W S. Stem cell culture engineering—process scale up and beyond. *Biotechnol J.* 2011; 6:1317-29.

Sheng, Z. H. and Q. Cai, Mitochondrial transport in neurons: impact on synaptic homeostasis and neurodegeneration. Nature Reviews Neuroscience 13, 77, 2012.

Shin, C. S., F. Lecanda, S. Sheikh, L. Weitzmann, S. L. Cheng, and R. Civitelli, Relative abundance of different cadherins defines differentiation of mesenchymal precursors into osteogenic, myogenic, or adipogenic pathways. Journal of Cellular Biochemistry 78, 566, 2000.

Shinmura D, Togashi I, Miyoshi S, Nishiyama N, Hida N, Tsuji H, et al. Pretreatment of human mesenchymal stem cells with pioglitazone improved efficiency of cardiomyogenic transdifferentiation and cardiac function. *Stem Cells.* 2011; 29:357-66.

Steinberg, M. S., On the mechanism of tissue reconstruction by dissociated cells. I. Population kinetics, differential adhesiveness. and the absence of directed migration. Proc Natl Acad Sci USA 48, 1577, 1962a.

Steinberg, M. S., On the mechanism of tissue reconstruction by dissociated cells, Iii. Free energy relations and the reorganization of fused, heteronomic tissue fragments. Proc Natl Acad Sci USA 48, 1769, 1962b.

Stroncek, D. F., M. Sabatino, J. Ren, L. England, S. A. Kuznetsov, H. G. Klein, and P. G. Robey, Establishing a bone marrow stromal cell transplant program at the national institutes of health clinical center. Tissue engineering Part B, Reviews 2014. DOI: 10.1089/ten.TEB.2013.0529

Sutlu T, Stellan B, Gilljam M, Quezada H C, Nahi H, Gahrton G, et al. Clinical-grade, large-scale, feeder-free expansion of highly active human natural killer cells for adoptive immunotherapy using an automated bioreactor. *Cytotherapy.* 2010; 12:1044-55.

Tigyi, G., D. L. Dyer, and R. Miledi, Lysophosphatidic acid possesses dual-action in cll-proliferation. Proc Natl Acad Sci USA 91, 1908, 1994.

Titushkin, I. and M. Cho, Modulation of cellular mechanics during osteogenic differentiation of human mesenchymal stem cells. Biophysical Journal 93, 3693, 2007.

Toma, C., W. R. Wagner, S. Bowry, A. Schwartz, and F. Villanueva, Fate Of culture-expanded mesenchymal stem cells in the microvasculature in vivo observations of cell kinetics. Circulation Research 104, 398, 2009.

Wagner, W., P. Horn, M. Castoldi, A. Diehlmann, S. Bork, R. Saffrich, V. Benes, J. Blake, S. Pfister, V. Eckstein, and A. D. Ho, Replicative senescence of mesenchymal stem cells: a continuous and organized process. Plos One 3(5):e2213, 2008.

Wei L, Fraser J L, Lu Z Y, Hu X, Yu S P. Transplantation of hypoxia preconditioned bone marrow mesenchymal stem cells enhances angiogenesis and neurogenesis after cerebral ischemia in rats. *Neurobiology of Disease.* 2012; 46:635-45.

Whitfield, M. J., W. C. J. Lee, and K. J. Van Vliet, Onset of heterogeneity in culture-expanded bone marrow stromal cells. Stem Cell Res 11, 1365, 2013.

Yeh, H. Y., B. H. Liu, and S. H. Hsu, The calcium-dependent regulation of spheroid formation and cardiomyogenic differentiation for MSCs on chitosan membranes. Biomaterials 33, 8943, 2012.

Ylostalo, J. H., Bartosh, T. J., Tiblow, A., & Prockop, D. J., Unique characteristics of human mesenchymal stromal/progenitor cells pre-activated in 3-dimensional cultures under different conditions. Cytotherapy, 16(11):1486-1500, 2014.

Ylostalo, J. H., T. J. Bartosh, K. Coble, and D. J. Prockop, Human Mesenchymal stem/stromal cells cultured as spheroids are self-activated to produce prostaglandin E2 that directs stimulated macrophages into an anti-inflammatory phenotype. Stem Cells 30, 2283, 2012.

Yu, Y. S., R. Dumollard, A. Rossbach, F. A. Lai, and K. Swann, Redistribution of mitochondria leads to bursts of ATP production during spontaneous mouse oocyte maturation. Journal of Cellular Physiology 224, 672, 2010.

Zhang, Q. Z., A. L. Nguyen, S. H. Shi, C. Hill, P. Wilder-Smith, T. B. Krasieva, and A. D. Le, Three-dimensional spheroid culture of human gingiva-derived mesenchymal stem cells enhances mitigation of chemotherapy-induced oral mucositis. Stem Cells and Development 21, 937, 2012.

Zhao F, Ma T. Perfusion bioreactor system for human mesenchymal stem cell tissue engineering: Dynamic cell seeding and construct development. *Biotechnol Bioeng.* 2005; 91:482-93.

Zhao, F., J. J. Veldhuis, Y. J. Duan, Y. Yang, N. Christoforou, T. Ma, and K. W. Leong, Low oxygen tension and synthetic nanogratings improve the uniformity and stemness of human mesenchymal stem cell layer. Molecular Therapy 18, 1010, 2010.

Zimmermann, J. A. and T. C. Mcdevitt, Pre-conditioning mesenchymal stromal cell spheroids for immunomodulatory paracrine factor secretion. Cytotherapy 16, 331, 2014.

I claim:

1. A method for expanding a stem cell, wherein said method comprises:
    culturing stem cells in a bioreactor system in the presence of thermally responsive microcarriers (TRMs), wherein stem cells adhere to the surface of said TRMs and wherein said TRMs are microcarrier beads coated with or comprising a thermally responsive material selected from one or more of poly(N-isopropylacrylamide) (PNIPAAm), poly(allylamine hydrochloride)-co-poly(N-isopropylacrylamide), and poly(styrene sulfonate)-co-poly(N-isopropylacrylamide);
    growing the adhered stem cells for a sufficient period of time for the stem cells to increase in numbers in the bioreactor system;
    detaching the stem cells from the TRMs by reducing the culture temperature to a critical solution temperature that results in said adhered cells detaching from the surface of said TRMs as cell clusters in the bioreactor system;
    providing said detached cell clusters sufficient time to aggregate and form three-dimensional (3D) stem cell aggregates in the bioreactor system, wherein said 3D stem cell aggregates exhibit improved therapeutic potency; and
    collecting said 3D aggregates and treating said 3D aggregates to dissociate said aggregates into individual cells in the bioreactor system, wherein the cells from said 3D cell aggregates exhibit one or more of the following: significantly upregulated C—X—C chemokine receptor type 4 (CXCR-4) expression relative to a stem cell cultured in the absence of the TRMs; and/or migration towards stromal cell-derived factor 1 (SDF-1).

2. The method according to claim 1, wherein said bioreactor system comprises a spinner flask bioreactor or a rocking platform bioreactor.

3. The method according to claim 1, wherein said culture conditions provide for rocking and/or agitation of said cells.

4. The method according to claim 1, wherein said dissociated TRMs comprise glass.

5. The method according to claim 1, wherein said TRMs optionally comprise a terminal coating of a layer of positively charged allylamine hydrochloride (PAH).

6. The method according to claim 1, wherein said TRMs have a diameter of between about 50 µm to about 500 µm.

7. The method according to claim 1, wherein said stem cells are cultured in said bioreactor under hypoxic or low oxygen conditions.

8. The method according to claim 7, wherein said hypoxic or low oxygen conditions comprise $O_2$ tension at between about 1% and about 10%.

9. The method according to claim 1, wherein said treating step comprises using an enzymatic agent.

10. The method according to claim 9, wherein said enzymatic agent is trypsin.

11. The method according to claim 1, wherein said stem cells are cultured in a container or vessel that comprises a surface or coating, wherein said surface or coating inhibits or prevents attachment of said stem cells to said container or vessel.

12. The method according to claim 1, wherein said dissociated cells are transplanted into a person or animal in need of treatment.

13. The method according to claim 1, wherein said stem cells are mesenchymal stem cells (MSC) from bone marrow.

14. The method according to claim 1, wherein said stem cells are mammalian or human stem cells.

15. The method according to claim 1, wherein said thermally responsive material is poly(N-isopropylacrylamide).

16. The method according to claim 1, wherein said thermally responsive material is poly(allylamine hydrochloride)-co-poly(N-isopropylacrylamide).

17. The method according to claim 1, wherein said thermally responsive material is poly(styrene sulfonate)-co-poly(N-isopropylacrylamide).

18. The method according to claim 1, wherein said microcarrier beads are coated with a thermally responsive material selected from one or more of poly(N-isopropylacrylamide) (PNIPAAm), poly(allylamine hydrochloride)-co-poly(N-isopropylacrylamide), and poly(styrene sulfonate)-co-poly(N-isopropylacrylamide).

19. The method according to claim 1, wherein said microcarrier beads comprise a thermally responsive material selected from one or more of poly(N-isopropylacrylamide) (PNIPAAm), poly(allylamine hydrochloride)-co-poly(N-isopropylacrylamide), and poly(styrene sulfonate)-co-poly(N-isopropylacrylamide).

* * * * *